United States Patent
Swanson et al.

[11] Patent Number: 6,070,094
[45] Date of Patent: May 30, 2000

[54] SYSTEMS AND METHODS FOR GUIDING MOVABLE ELECTRODE ELEMENTS WITHIN MULTIPLE-ELECTRODE STRUCTURES

[75] Inventors: David K. Swanson, Mountain View; Dorin Panescu, Sunnyvale; James G. Whayne, Saratoga, all of Calif.

[73] Assignee: EP Technologies, Inc., Sunnyvale, Calif.

[21] Appl. No.: 09/258,653

[22] Filed: Feb. 26, 1999

Related U.S. Application Data

[60] Continuation of application No. 08/954,276, Oct. 21, 1997, Pat. No. 5,876,336, which is a division of application No. 08/679,156, Jul. 12, 1996, Pat. No. 5,722,402, which is a continuation of application No. 08/320,301, Oct. 11, 1994, abandoned.

[51] Int. Cl.[7] ............................ A61B 5/0408; A61B 8/08; A61B 8/12; A61B 18/14; A61N 1/05
[52] U.S. Cl. ......................... 600/374; 600/439; 600/467; 600/509; 606/34; 606/41; 607/122
[58] Field of Search .................................... 600/374, 439, 600/467, 509; 128/899; 607/122, 126; 606/41, 45, 49, 34

[56] References Cited

U.S. PATENT DOCUMENTS

| | | |
|---|---|---|
| 4,522,212 | 6/1985 | Gelinas et al. . |
| 4,628,937 | 12/1986 | Hess et al. . |
| 4,649,924 | 3/1987 | Taccardi . |
| 4,674,518 | 6/1987 | Salo . |
| 4,699,147 | 10/1987 | Chilson et al. . |
| 4,706,681 | 11/1987 | Breyer et al. ............................ 600/374 |
| 4,852,580 | 8/1989 | Wood . |
| 5,058,583 | 10/1991 | Geddes et al. . |
| 5,092,339 | 3/1992 | Gedes et al. . |
| 5,156,151 | 10/1992 | Imran . |
| 5,282,840 | 2/1994 | Hudrlik . |
| 5,297,549 | 3/1994 | Beatty et al. . |
| 5,309,910 | 5/1994 | Edwards et al. . |
| 5,311,873 | 5/1994 | Savard et al. . |
| 5,323,781 | 6/1994 | Ideker et al. . |
| 5,324,234 | 6/1994 | Imran . |
| 5,327,889 | 7/1994 | Imran . |
| 5,341,807 | 8/1994 | Nardella . |
| 5,383,917 | 1/1995 | Desai et al. . |
| 5,385,148 | 1/1995 | Lesh et al. .............................. 600/439 |
| 5,391,199 | 2/1995 | Ben-Haim . |
| 5,409,000 | 4/1995 | Imran . |
| 5,411,025 | 5/1995 | Webster, Jr. . |
| 5,433,198 | 7/1995 | Desai . |
| 5,450,846 | 9/1995 | Goldreyer . |
| 5,465,717 | 11/1995 | Imran et al. . |
| 5,476,495 | 12/1995 | Kordis et al. . |
| 5,487,391 | 1/1996 | Panescu . |
| 5,697,377 | 12/1997 | Wittkampf . |

FOREIGN PATENT DOCUMENTS

| | | |
|---|---|---|
| 0 339 536 A1 | 11/1990 | European Pat. Off. . |
| 0 659 388 | 12/1993 | European Pat. Off. . |

Primary Examiner—Lee Cohen
Attorney, Agent, or Firm—Lyon & Lyon LLP

[57] ABSTRACT

Systems and related methods guide a movable electrode within an array of multiple electrodes located within the body. The systems and methods employ the movable electrode or at least one of the multiple electrodes on the array to generate and then sense electrical or sonic energy in a predetermined fashion to generates an output that locates the movable electrode within the array.

22 Claims, 18 Drawing Sheets

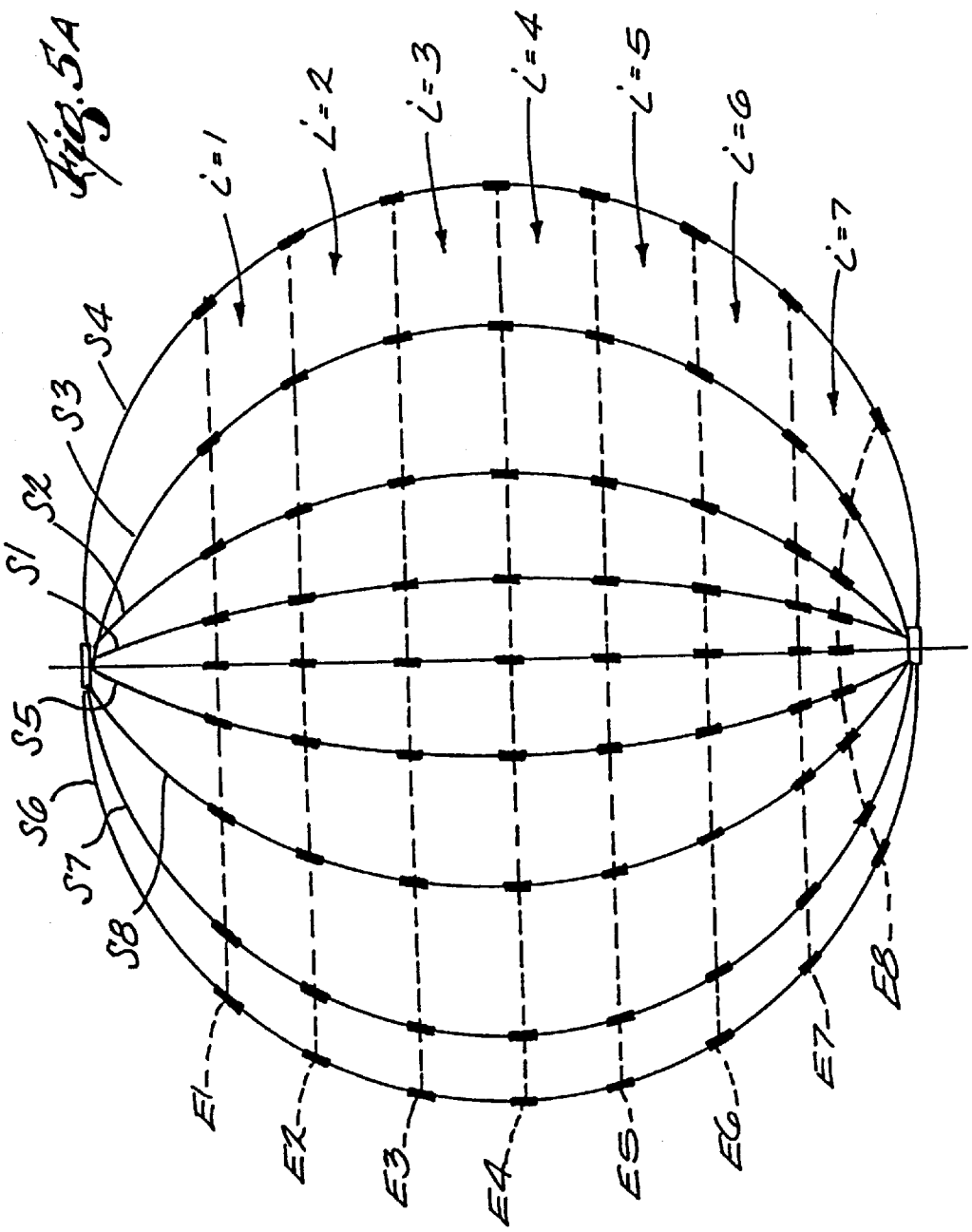

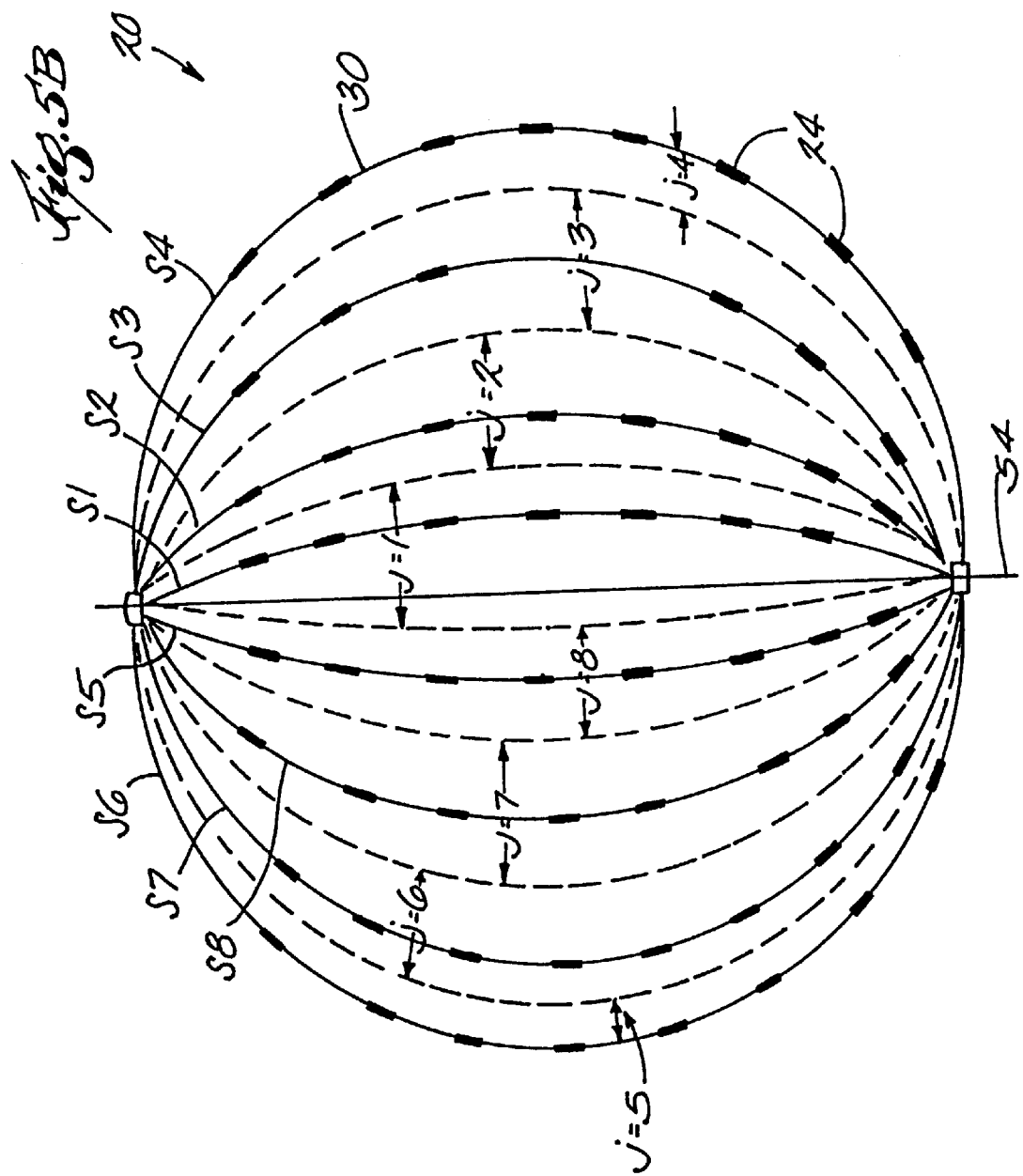

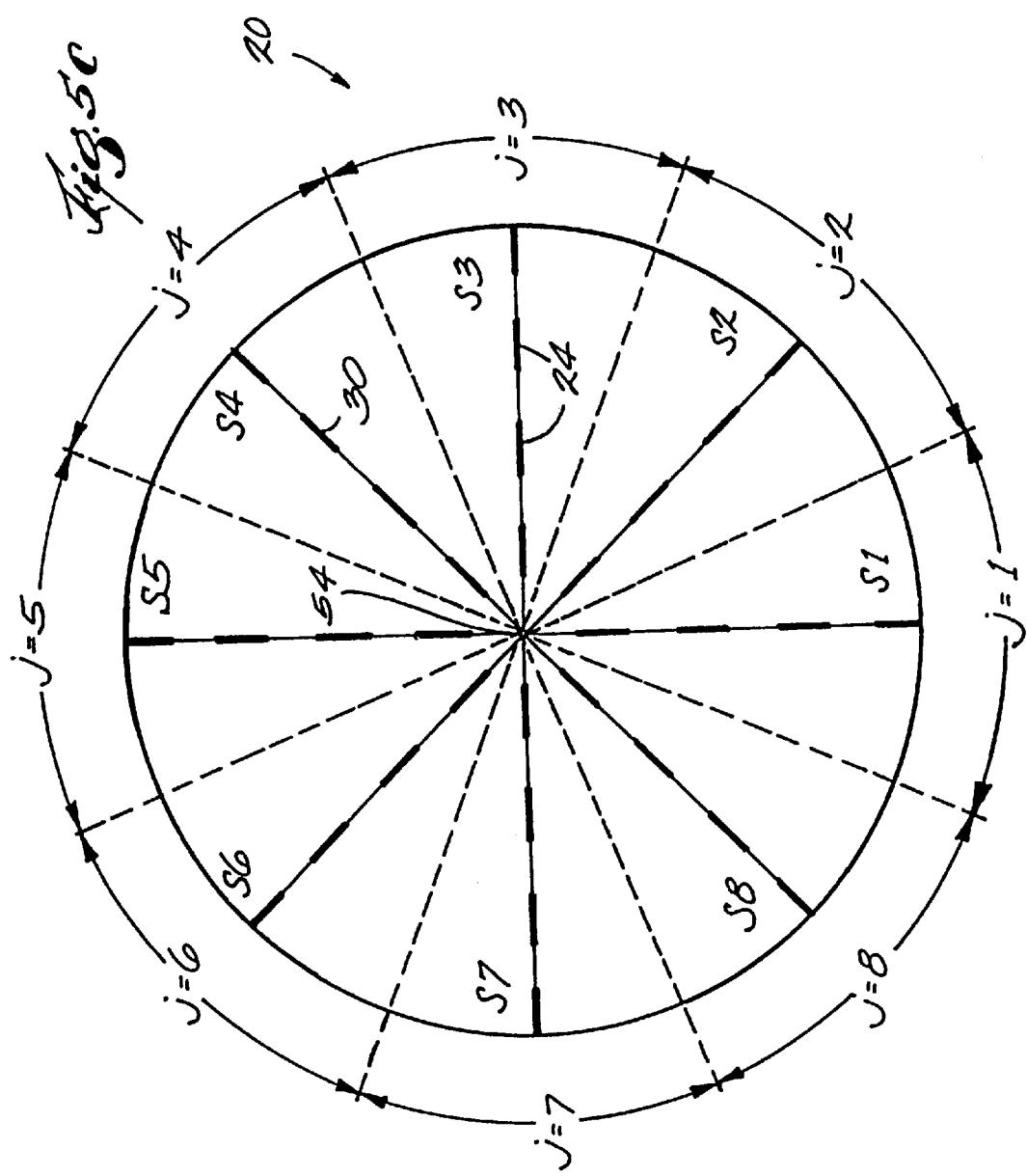

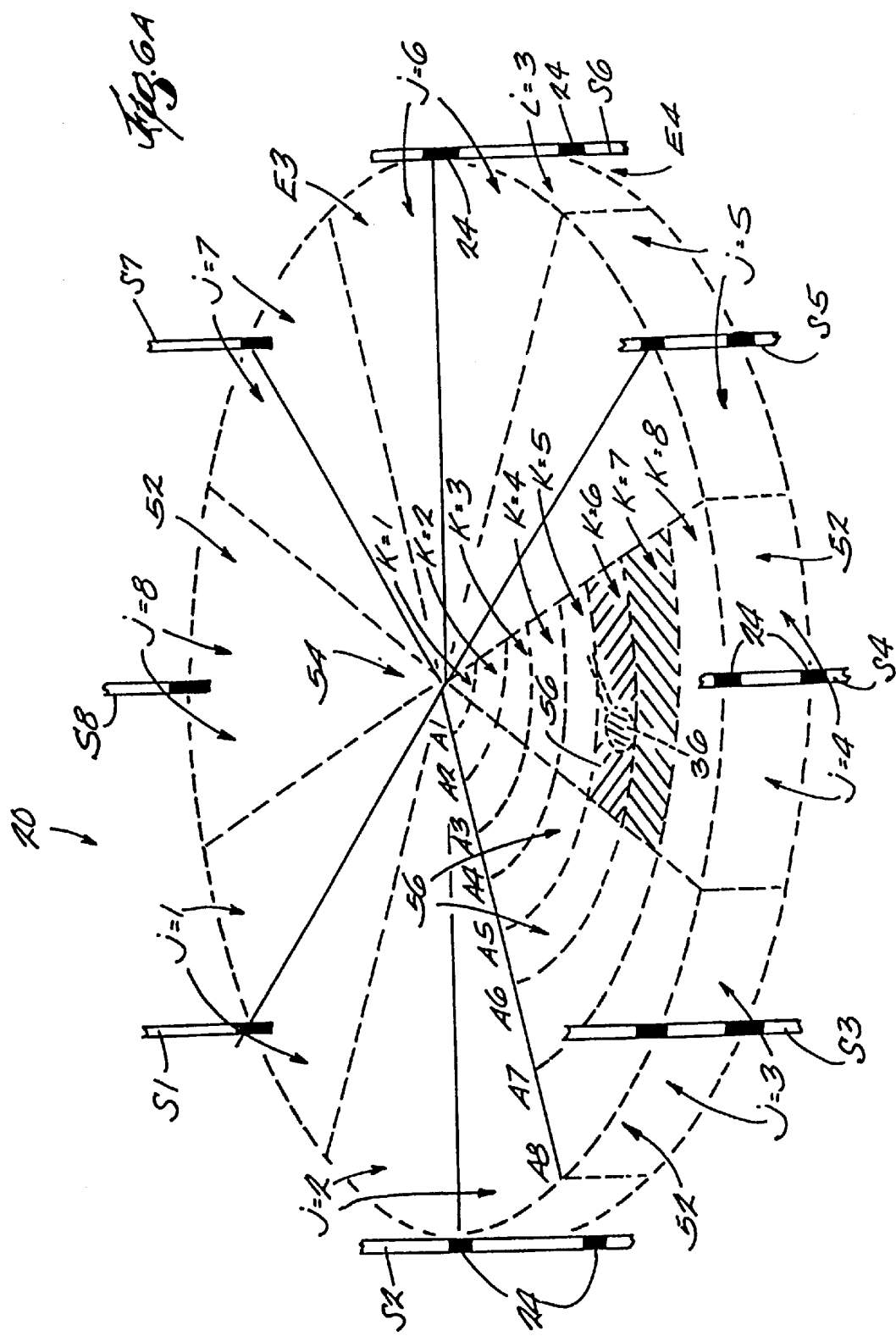

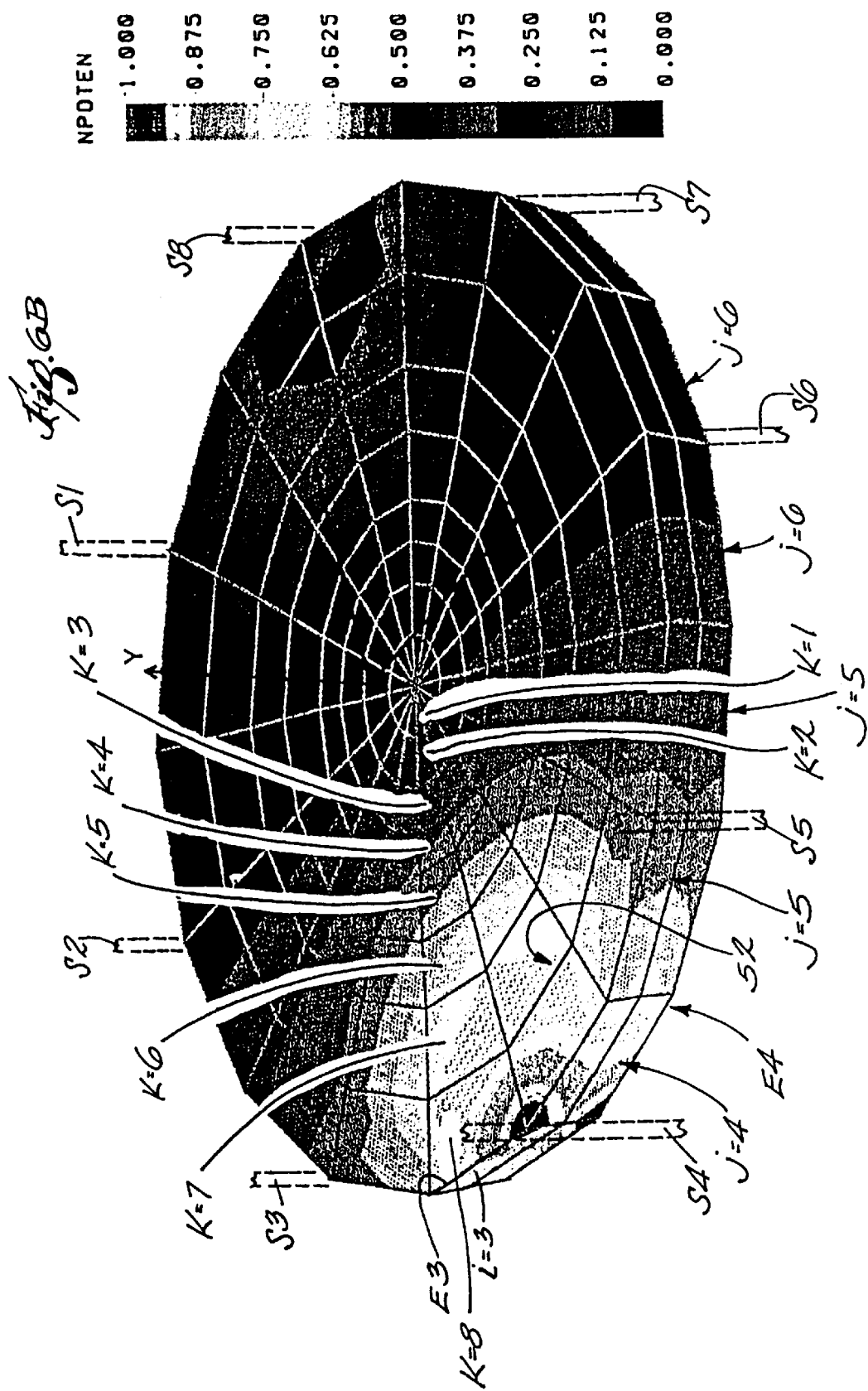

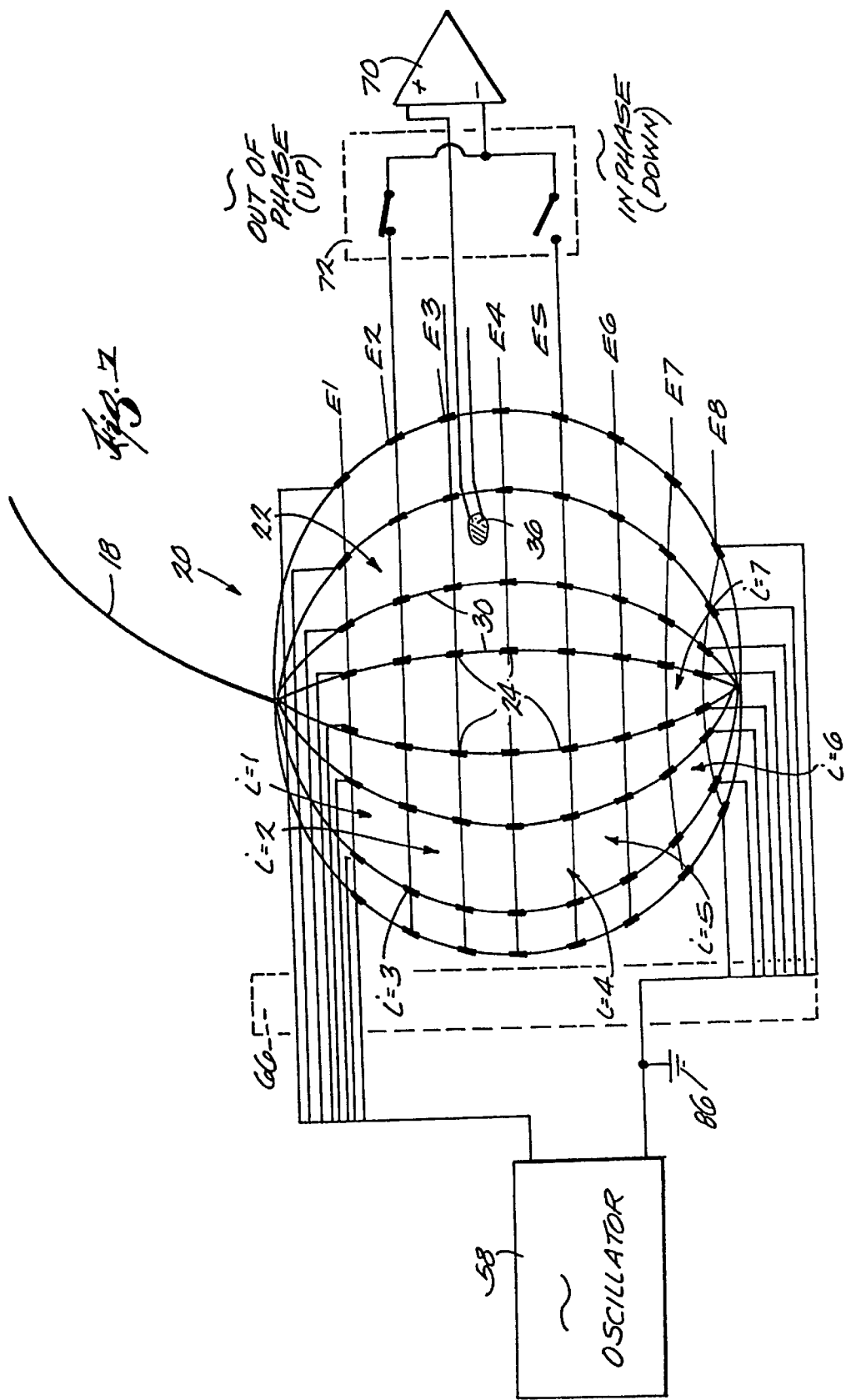

DISTANCE BETWEEN ABLATION ELECTRODE
AND
TARGETED ABLATION SITE

SYSTEMS AND METHODS FOR GUIDING MOVABLE ELECTRODE ELEMENTS WITHIN MULTIPLE-ELECTRODE STRUCTURES

This is a continuation of application Ser. No. 08/954,276, filed Oct. 21, 1997 (now U.S. Pat. No. 5,876,336), which is a divisional of application Ser. No. 08/679,156, filed Jul. 12, 1996 (now U.S. Pat. No. 5,722,402), which is a continuation of application Ser. No. 08/320,301, filed Oct. 11, 1994 (now abandoned), all of which are hereby expressly and fully incorporated and fully incorporated herein by reference.

FIELD OF THE INVENTION

The invention generally relates to systems and methods for guiding or locating diagnostic or therapeutic electrode elements in the interior regions of the body. More particularly, the invention relates to guiding or locating diagnostic or therapeutic electrode elements inside the heart for treatment of cardiac conditions.

BACKGROUND OF THE INVENTION

Physicians make use of catheters today in medical procedures to gain access into interior regions of the body for diagnostic and therapeutic purposes. It is important for the physician to be able to precisely position the catheter within the body to gain contact with a desired tissue location.

The need for precise control over the catheter is especially critical during procedures that ablate myocardial tissue from within the heart. These procedures, called ablation therapy, are used to treat cardiac rhythm disturbances.

During these procedures, a physician steers catheter through a main vein or artery into the interior region of the heart that is to be treated. The physician then further manipulates a steering mechanism to place the electrode carried on the distal tip of the catheter into direct contact with the endocardial tissue. The physician directs energy from the electrode through myocardial tissue either to an indifferent electrode (in a uni-polar electrode arrangement) or to an adjacent electrode (in a bi-polar electrode arrangement) to ablate the tissue.

Before ablating heart tissue, physicians often examine the propagation of electrical impulses in heart tissue to locate aberrant conductive pathways and to identify the arrhythmia foci, which are ablated. The techniques used to analyze these pathways and locate foci are commonly called "mapping."

Conventional cardiac tissue mapping techniques use multiple electrodes positioned in contact with heart tissue to obtain multiple electrograms. These conventional mapping techniques require invasive open heart surgical techniques to position the electrodes on the interior or exterior surfaces of the heart.

An alternative technique of introducing multiple-electrode arrays into the heart through venous or arterial accesses to map myocardial tissue is known. Compared to conventional, open heart mapping techniques, endocardial mapping techniques, being comparatively non-invasive, hold great promise. Multiple electrogram signals obtained from within the heart can be externally processed to detect local electrical events and identify likely foci.

Once mapping identifies the foci, an ablation electrode is steered into position in contact with a focus site. At least, in theory, this is the goal sought to be achieved. In actuality, though, the task of remotely guiding an ablation element within the blood pool of a beating heart to a particular focus site can be, at best, problematic.

There is the need to provide simple, yet reliable, ways of guiding electrode elements within the heart, or within other interior parts of the body, to precise locations targeted for diagnosis or treatments.

SUMMARY OF THE INVENTION

This invention has as its principal objective the realization of safe and efficacious systems and methods for remotely locating electrode elements at precise locations within the body.

One aspect of the invention provides a system and related method for guiding a movable electrode within an array of multiple electrodes located within the body. The system and method couple an emitting electrode to an electrical energy generating element. The emitting electrode comprises either the movable electrode or at least one of the electrodes in the array. The generating element conditions the emitting electrode to emit electrical energy while the movable electrode is located within the array.

According to this aspect of the invention, the system and method couple a sensing electrode to a sensing element. The sensing electrode comprises either the movable electrode or at least one of the electrodes in the array. The sensing element conditions the sensing electrode to sense electrical energy emitted by the emitting electrode.

Further in accordance with this aspect of the invention, the system and method couple a processing element to the sensing element. The processing element analyzes sensed electrical energy and generates, based upon its analysis, an output that locates the movable electrode within the array.

Another aspect of the invention provides a system and method for ablating tissue within the heart. The system and method are usable in conjunction with an array of multiple electrodes located within the heart to locate foci appropriate for ablation and an ablation electrode that is movable within the array for applying ablating energy to the foci.

According to this aspect of the invention, the system and method condition an emitting electrode to emit electrical energy while the ablation electrode is present within the array. The emitting electrode comprises either the ablation electrode or at least one of the electrodes in the array. While the ablation electrode is present within the array, the system and method also sense the emitted electrical energy with a sensing electrode The sensing electrode comprises either the ablation electrode or at least one of the electrodes in the array. The system and method process the sensed electrical energy to generate an output locating the ablation electrode relative to the multiple electrodes on the array.

In a preferred embodiment, the system and method continuously generate the location-indicating output while the physician moves the ablation electrode within the array. In this way, the system and method aid the physician in guiding the ablation electrode to the targeted ablation site.

In a preferred embodiment, the systems and methods that incorporate either aspect of the invention generate an electric field within the array, while sensing electrode electric potentials in the electric field. In this embodiment, the processing element generates the output by analyzing spatial variations in the electrical potentials within the array. The variations can comprise variations in phase, variations in amplitude, or both. Alternatively, the processing element generates the output by analyzing spatial variations in impedances between the emitting and sensing electrodes.

In a preferred embodiment, the systems and methods that incorporate either aspect of the invention inject electrical energy into body tissue, while sensing tissue response to the injected electrical energy. In this embodiment, the processing element generates the output by analyzing differences in the sensed tissue response. In one implementation, the processing element analyzes time differences in the sensed tissue response. In another implementation, the sensing element senses the depolarization of myocardial tissue, and the processing element analyses time differences in sensed tissue depolarization.

Yet another aspect of the invention provides a system and method for ablating tissue within the heart. The system and method locate an array of multiple electrodes in contact with tissue within the heart to sense electrical activity in heart tissue to locate foci appropriate for ablation. The system and method also locates a movable ablation electrode within the array. The system and method condition an emitting electrode comprising either the ablation electrode or at least one of the electrodes in the array to emit ultrasonic energy while the ablation electrode is located within the array. While the ablation electrode is located within the array, the system and method also sense the emitted ultrasonic energy with a sensing electrode. The sensing electrode comprises the ablation electrode, if the ablation electrode is not the emitting electrode, or, otherwise, at least one of the electrodes in the array. The system and method process the sensed ultrasonic energy to generate an output locating the ablation electrode relative to the multiple electrodes in the array.

In a preferred embodiment of this aspect of the invention, the system and method move the ablation electrode within the array while repeating the emitting, sensing, and processing steps just described. The result is an output that continuously locates the ablation electrode as it moves within the array.

Other features and advantages of the inventions are set forth in the following Description and Drawings, as well as in the appended claims.

BRIEF DESCRIPTION OF THE DRAWINGS

FIG. 5A is a schematic side view of the multiple-electrode structure shown in FIG. 2 showing the i-indexing used to point to the location of the ablation electrode within the multiple-electrode structure;

FIGS. 5B and 5C are schematic views of the multiple-electrode structure shown in FIG. 2 showing the i-indexing used to point to the location of the ablation electrode within the multiple-electrode structure, FIG. 5B being a schematic side view and FIG. 5C being a schematic top view;

FIG. 6A is a schematic perspective view of the mid-portion of the multiple-electrode structure shown in FIG. 2 showing the i, j, and k-indexing used to point to the location of the ablation electrode within the multiple-electrode structure;

FIG. 6B is a schematic view of a normalized iso-voltage array within the mid-portion of the multiple basket structure, like that shown in FIG. 6A, when the ablation electrode is located in the region pointed by the indices (i=3, j=4), and the correlation of the iso-voltage array to the k indices within that region;

FIG. 7 is a schematic view of the use of the element shown in FIG. 4 for determining the i index;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
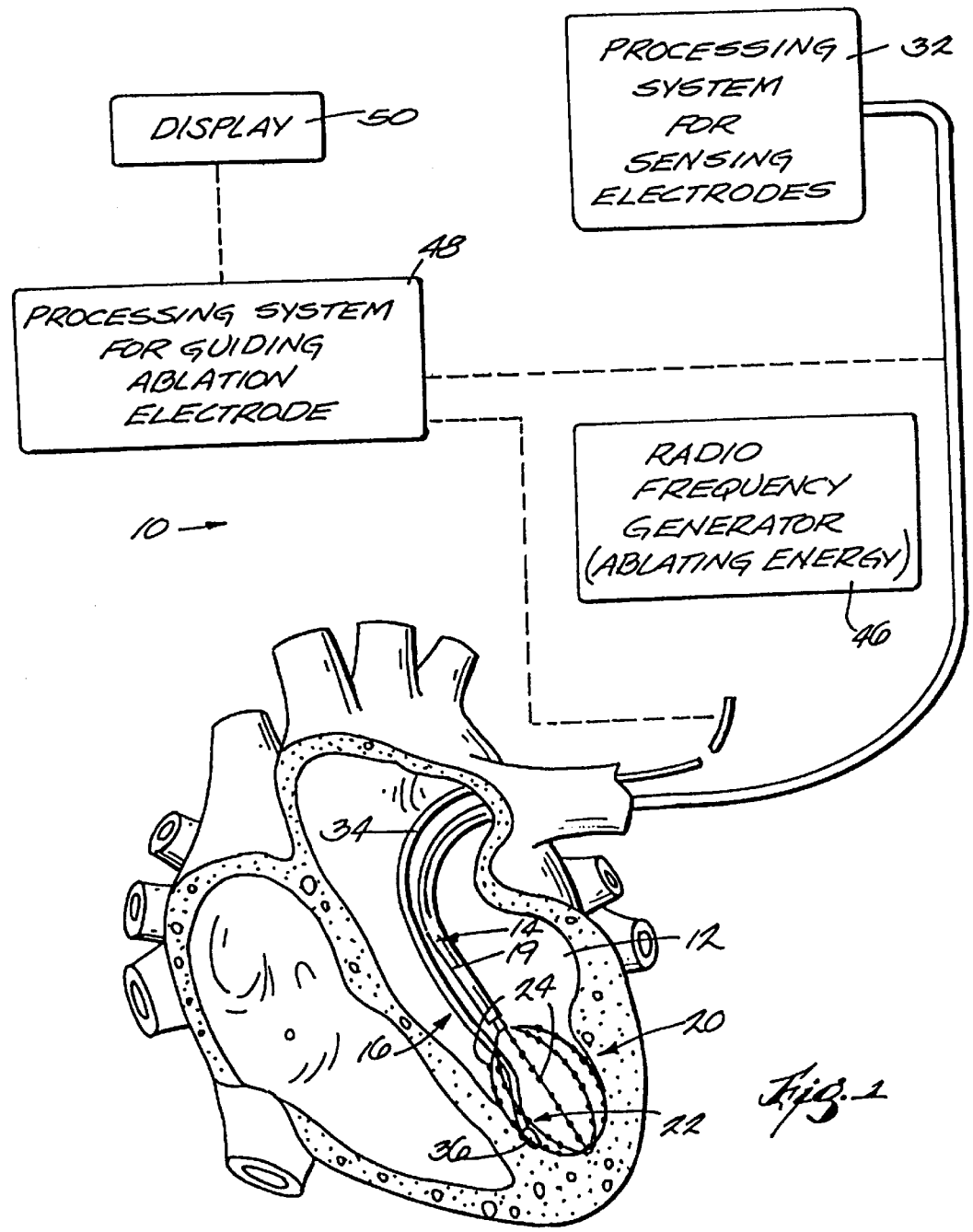
FIG. 1 is a system, which embodies the features of the invention, for accessing a targeted tissue region in the body for diagnostic or therapeutic purposes.

FIG. 1 shows the components of a system 10 for accessing a targeted tissue region in the body for diagnostic or therapeutic purposes. The illustrated embodiment shows the system 10 being used for ablating heart tissue. This is because the invention is well suited for use in this application.

Still, it should be appreciated that the invention is applicable for use in other tissue ablation applications. For example, the various aspects of the invention have application in procedures for ablating tissue in the prostrate, brain, gall bladder, uterus, and other regions of the body, using systems that are not necessarily catheter-based.

FIG. 1 shows the system 10 deployed and ready for use within a selected region 12 inside a human heart. FIG. 1 generally shows the system 10 deployed in the left ventricle of the heart. Of course, the system 10 can be deployed in other regions of the heart, too. It should also be noted that the heart shown in the FIG. 1 is not anatomically accurate. FIG. 1 shows the heart in diagrammatic form to demonstrate the features of the invention.

The system 10 includes a mapping probe 14 and an ablation probe 16. In FIG. 1, each is separately introduced into the selected heart region 12 through a vein or artery (typically the femoral vein or artery) through suitable percutaneous access. Alternatively, the mapping probe 14 and ablation probe 16 can be assembled in an integrated structure for simultaneous introduction and deployment in the heart region 12.

Further details of the deployment and structures of the probes 14 and 16 are set forth in pending U.S. patent application Ser. No. 08/033,641, filed Mar. 16, 1993, entitled "Systems and Methods Using Guide Sheaths for Introducing, Deploying, and Stabilizing Cardiac Mapping and Ablation Probes."

I. The Mapping Probe

The mapping probe 14 has a flexible catheter body 18. The distal end of the catheter body 18 carries a three dimensional multiple-electrode structure 20. In the illustrated embodiment, the structure 20 takes the form of a basket defining an open interior space 22 (see FIG. 2). It should be appreciated that other three dimensional structures could be used.

Figure 2:
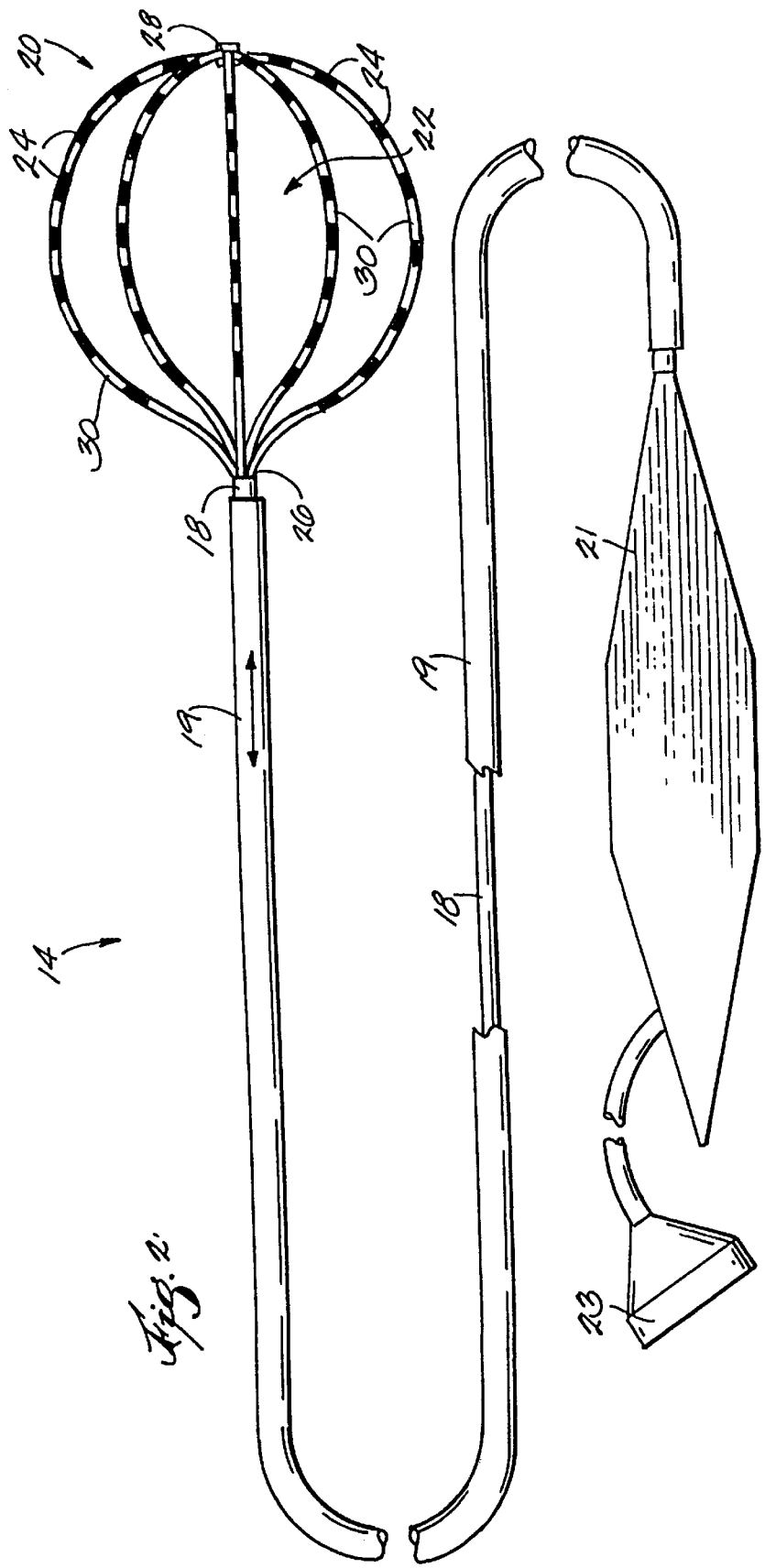
FIG. 2 is an enlarged perspective view of a multiple-electrode structure used in association with the system shown in FIG. 1.

As FIG. 2 shows, the illustrated basket structure 20 comprises a base member 26 and an end cap 28. Generally flexible splines 30 extend in a circumferentially spaced relationship, between the base member 26 and the end cap 28.

The splines 30 are preferably made of a resilient inert material, like Nitinol metal or silicone rubber. The splines 30 are connected between the base member 26 and the end cap 28 in a resilient, pretensed condition, to bend and conform to the endocardial tissue surface they contact. In the illustrated embodiment (see FIG. 2), eight splines 30 form the basket structure 20. Additional or fewer splines 30 could be used.

The splines 30 carry an array of electrodes 24. In the illustrated embodiment, each spline 30 carries eight electrodes 24. Of course, additional or fewer electrodes 24 can be used.

A slidable sheath 19 is movable along the axis of the catheter body 18 (shown by arrows in FIG. 2). Moving the sheath 19 forward causes it to move over the basket structure 20, collapsing it into a compact, low profile condition for introducing into the heart region 12. Moving the sheath 19 rearward frees the basket structure 20, allowing it to spring open and assume the pretensed position shown in FIG. 2.

Further details of the basket structure are disclosed in pending U.S. patent application Ser. No. 08/206,414, filed Mar. 4, 1994, entitled "Multiple Electrode Support Structures."

The electrodes 24 are electrically coupled to a processing system 32 (see FIG. 1). A signal wire (not shown) is electrically coupled to each electrode 24. The wires extend through the body 18 of the probe 14 into a handle 21, in which they are coupled to an external multiple pin connector 23. The connector 23 electrically couples the electrodes to the processing system 32 (and the processing element 48, as will be described later in greater detail).

The electrodes 24 sense electrical activity in heart tissue. The sensed activity is processed by the processing system 32 to assist the physician in identifying the site or sites within the heart appropriate for ablation.

This process, called mapping, can be accomplished in various way, according to the choice of the physician.

For example, the physician can condition the processing system 32 to take multiple, sequential measurements of the transmission of electrical current by heart tissue to obtain tissue resistivity measurements. The processing of tissue resistivity signals to identify appropriate ablation sites is disclosed in co-pending U.S. patent application Ser. No. 08/197,236, filed Jan. 28, 1994, and entitled "Systems and Methods for Matching Electrical Characteristics and Propagation Velocities in Cardiac Tissue to Locate Potential Ablation Sites."

Alternatively, or in conjunction with tissue resistivity measurements, the physician can condition the processing system 32 to acquire and process electrograms in a conventional fashion. The processing system 32 processes the electrogram information to map the conduction of electrical impulses in the myocardium.

In either situation, the processing system 32 processes the sensed information to derive the location of a site appropriate for ablation, using the probe 16.

II. The Ablation Probe

The ablation probe 16 (see FIG. 3A) includes a flexible catheter body 34 that carries one or more ablation electrodes 36. For the sake of illustration, FIG. 3A shows a single ablation electrode 36 carried at the distal tip of the catheter body 34. Of course, other configurations employing multiple ablation electrodes are possible, as described in pending U.S. patent application Ser. No. 08/287,310, filed Aug. 8, 1994, entitled "Systems and Methods for Ablating Heart Tissue Using Multiple Electrode Elements."

A handle 38 is attached to the proximal end of the catheter body 34. The handle 38 and catheter body 34 carry a steering mechanism 40 for selectively bending or flexing the catheter body 34 along its length, as the arrows in FIG. 3A show.

Figure 3:
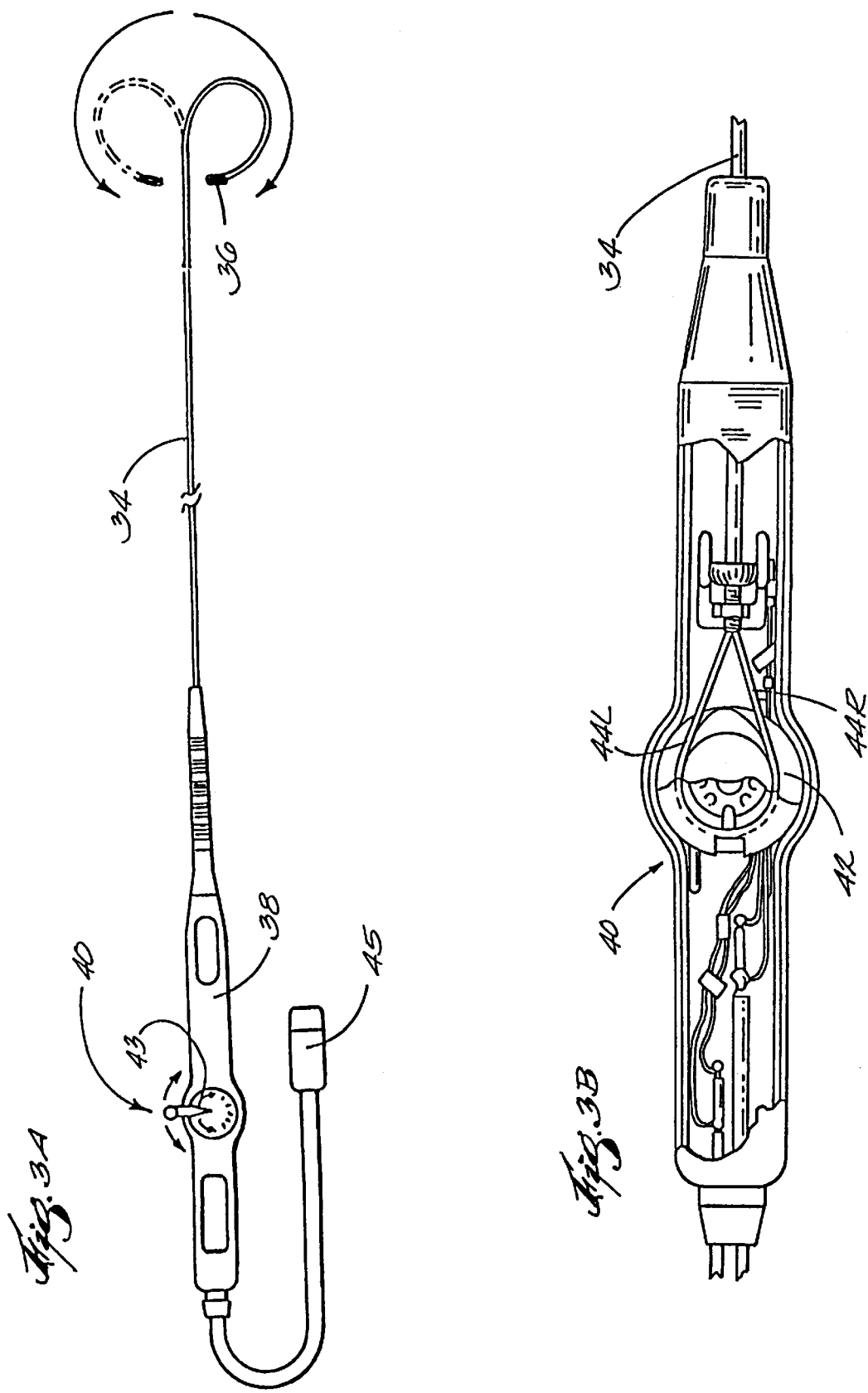
FIGS. 3A and 3B are an enlarged view of an ablation probe and its steering mechanism used in association with the system shown in FIG. 1.

The steering mechanism 40 can vary. In the illustrated embodiment (see FIG. 3B), the steering mechanism 40 includes a rotating cam wheel 42 with an external steering lever 43 (which FIG. 3A shows). As FIG. 3 shows, the cam wheel 42 holds the proximal ends of right and left steering wires, designated 44R and 44L. The wires 44R and 44L pass through the catheter body 34 and connect to the left and right sides of a resilient bendable wire or spring (not shown) at the distal end of the body 34.

Movement of the steering lever flexes the distal end of the body 34 to bring the electrode 36 into conforming, intimate contact against the endocardial tissue.

Further details of the steering mechanism are shown in U.S. Pat. No. 5,254,088, which is incorporated herein by reference.

A wire (not shown) electrically connected to the ablation electrode 36 extends through the catheter body 34 into the handle 38, where it is electrically coupled to an external connector 45. The connector 45 connects the electrode 36 to a generator 46 of ablation energy (and to the processing element 48, as will be described later in greater detail) (see FIG. 1). The type of energy used for ablation can vary. Typically, the generator 46 supplies electromagnetic radio frequency energy, which the electrode 36 emits into tissue.

In use, the physician places the ablation electrode 36 in contact with heart tissue at the site identified by the mapping probe 14 for ablation. The ablation electrode emits ablating energy to heat and thermally destroy the contacted tissue.

III. The Ablation Probe Guiding system

As FIG. 1 shows, the system 10 includes a processing element 48 electrically coupled to the mapping probe 14 and the ablation probe 16. The element 48 collects and processes information regarding the location of the ablation probe 16 within the space 22 defined by the basket structure 20, in term of its position relative to the position of the electrodes 24. The processing element provides a position-identifying output that aids the physician in guiding the ablation electrode 36 into contact with tissue at the site identified for ablation.

In the illustrated and preferred embodiment, the element 48 includes an output display device 50 (e.g., a CRT, LED display, or a printer). The device 50 preferably presents the position-identifying output in a real-time format most useful to the physician for remotely guiding the ablation electrode 36 within the basket structure 20.

The processing element 48 can process and provide position-specific information in various ways. Representative modes of operation for the element 48 will now be described.

A. Voltage Phase/Amplitude Mode

Figure 4:
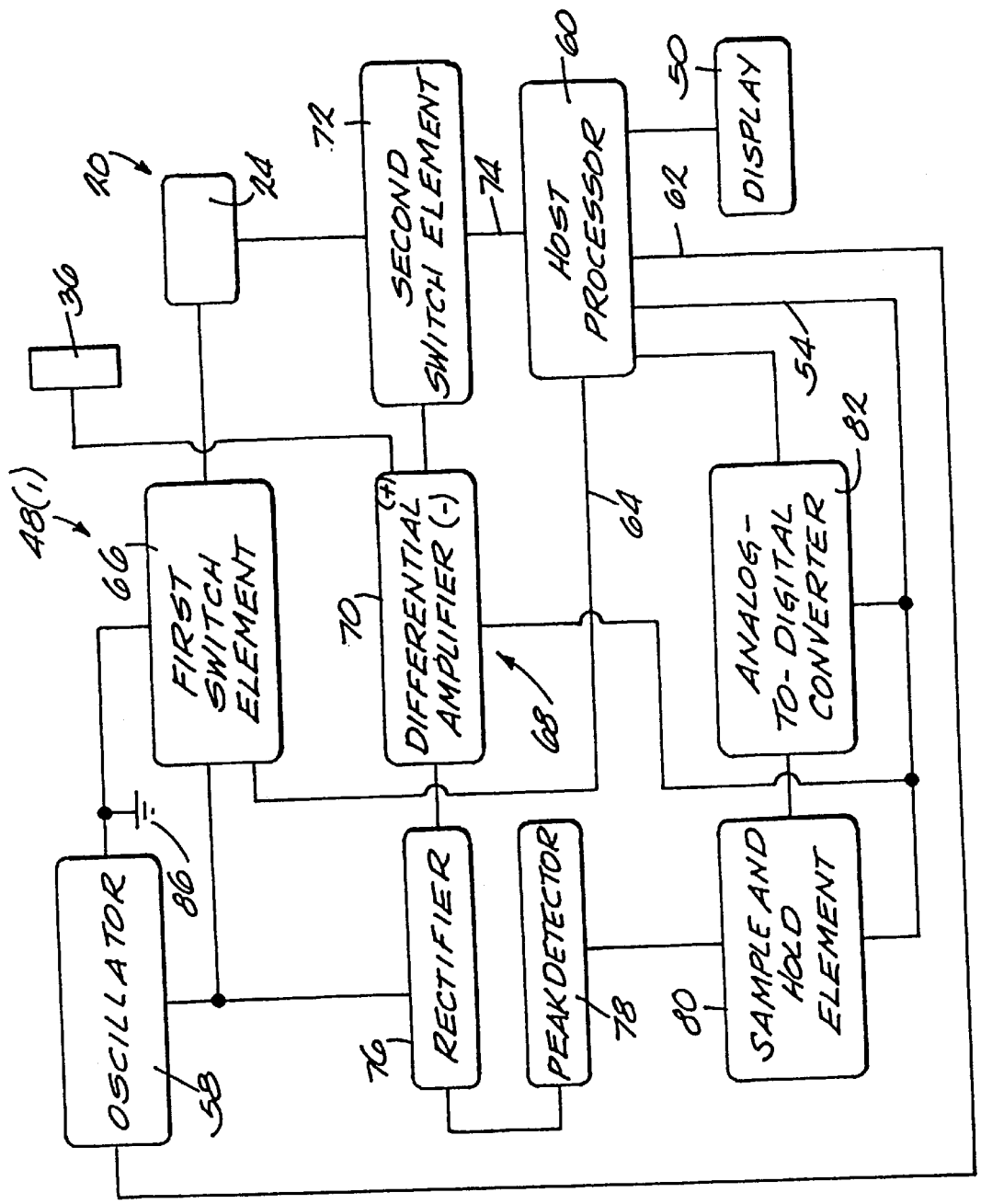
FIG. 4 is a schematic view of an element for determining the location of an ablation electrode within a multiple-electrode structure using phase/amplitude sensing.

FIG. 4 shows one preferred implementation of the processing element, designated 48(1). In this implementation, the element 48(1) generates an electrical field within the interior space 22 of the basket structure 20. The element 48(1) senses the phase and amplitude of the electrical potentials to provide position-specific output regarding the position of the ablation electrode 36.

As FIGS. 5A/B/C and 6 show, the element 48(1) expresses the position-specific output in terms of a three dimensional discrete coordinate system having an i index, a j index; and a k index. The i, j, and k indices point to the location of the ablation electrode 36 within the three dimensional discretized space 22 bounded by the basket structure 20.

The i index points to horizontal sectors of space between adjacent horizontal sets of electrodes 24, which are designated E1 to E8 in FIG. 5A. In the illustrated embodiment (see FIG. 5A), the i index points to one of 7 horizontal sectors (i=1 to i=7). The index i=1 points to the sector between the topmost set of electrodes 24 (E1) and the adjacent set of electrodes 24 (E2). The index i=2 points to the sector between the second and third topmost sets of electrodes 24 (i.e., between E2 and E3), and so on, with the index i=7 pointing to the sector between the two bottommost sets of electrodes 24 (i.e., between E7 and E8).

The vertical spacing between the electrode sets E1 to E8, and therefore the vertical range of each i-index sector, can be physically increased or decreased, depending upon the degree of precision desired. Also, the space between adjacent sets of electrodes can be further subdivided electronically for greater resolution. This implementation uses look-up tables based upon signed normalized voltage amplitudes to determine position within the space between adjacent sets.

As FIGS. 5B and 5C show, the j index points to arcuate sectors of space, each being symmetrically bisected by a spline 30, which are designated 51 to 58 in FIG. 5B. The sectors extend radially out from the center axis 54 of the basket structure 24, with each sector spanning an angle of $2\pi/n$ measured about the center axis 54, where n equals the number of splines.

In the illustrated embodiment, the j index points to one of 8 arcuate sectors (j=1 to j=8). The index j=1 points to the sector symmetrically bisected by spline S1. The index j=2 points to the next circumferential sector symmetrically bisected by spline S2, and so on, with the index j=8 pointing to the sector symmetrically bisected by spline S8.

The physical number and circumferential spacing of splines determine the span angle, and therefore the size of each j-index sector. These can be increased or decreased electronically, depending upon the degree of resolution desired. For example, the span angle can be halved by determining which is the second-closest spline.

As FIG. 6A shows, the values assigned to the indices i and j point to one of several pie-shaped regions 52 within the basket structure 20 contained within the space defined by the intersection of a given spherical sector (pointed to by the j index) and the a given horizontal sector (pointed to by the i index). The dimension of the region 52 depends upon the horizontal and circumferential spacing among electrodes 24.

The k index further delimits one of several zones 56 within the region 52. The k index locates the zone 56 in terms of a radial distance from the center axis 54 of the basket structure 20. The zone 56 lies along an arc within the region 52 spaced radially from the center axis 54 at a distance prescribed by the k index.

Together, a given set of i, j, and k indices place the ablation electrode 36 within the space lying along one of the zones 56 (the k index) within one of the regions 52 (the i index and the j index).

Referring back to FIG. 4, the element 48(1) includes an oscillator 58. A host processor 60 coupled to the oscillator 58 by a control bus 62 conditions the oscillator 58 to generate an AC wave form at a predetermined amplitude and frequency.

The selected current amplitude of the output of the oscillator 58 can vary between 0.1 mAmp to about 5 mAmp. The frequency selected can also vary from about 5 kHz to about 100 kHz. Currents substantially above about 5 mAmp and frequencies substantially below 5 kHz should be avoided, as they pose the danger of inducing fibrillation.

The shape of the wave form can also vary. In the illustrated and preferred embodiment, the wave form is sinusoidal. However, square wave shapes or pulses can also be used, although harmonics may be encountered if capacitive coupling is present.

Furthermore, the wave form need not be continuous. The oscillator 58 may generate pulsed wave forms.

An address bus 64 couples the host processor 60 to a first electronic switch element 66, which is, in turn, coupled to each electrode 24. The host processor 60 conditions the first switch element 66 to distribute the AC output of the oscillator 58 in a prescribed fashion in parallel to one or more electrodes 24.

The element 48(1) also includes a data acquisition system 68. The system 68 includes a differential amplifier 70. The ablation electrode 36 is coupled to the noninverting input of the amplifier 70.

A second electronic switch element 72 is independently coupled to each electrode 24. The host processor 60 conditions the second switch element 72 via a second address bus 74 to couple one selected electrode 24 on the array to the inverting input of the amplifier 70.

In this arrangement, the differential amplifier 70 reads the electrical potential of the ablation electrode 36 with respect to that of the electrode 24 then coupled to the amplifier 70 by the switch element 72. The output of the amplifier 70 is an AC voltage signal.

The data acquisition system 68 also includes a synchronized rectifier 76 and peak detector 78. The rectifier 76 receives the AC signal voltage output of the amplifier 70 and senses its phase relative to the phase at the output of the oscillator 58. The detector 78 determines the peak amplitude of the AC voltage signal output of the amplifier 70. In an alternative implementation, the rectifier 76 and detector 78 can take the form of a synchronized phase detector, or any other element that detects phase and amplitude (whether as an RMS value, peak value, average rectified value, or otherwise).

The output of the detector 78 is an analog signal having a value corresponding to the peak amplitude of the AC output of the amplifier 70, and a sign (+ or −) denoting whether the AC voltage output is in phase with the oscillator 58 (+) or out of phase with the oscillator 58 (−).

The data acquisition system 68 registers this analog signal in association with the electrode 24 then-coupled to the amplifier 70 in a sample and hold element 80. An analog to digital converter 82 converts the analog signals to digital signals for processing by the host processor 60. A suitable control bus 54 couples the sample and hold element 80, converter 82, and differential amplifier 70 to the host processor 60 for coordination and control functions. For example, the host processor 60 can set the sampling rate of the sample and hold element 80, the input range of the converter 82, and the amplification of the amplifier 70.

(i) Determining the i Index

In determining the i index of the ablation element 36 (see FIG. 7), the host processor 60 conditions the first switch element 66 to connect the bottommost electrode set E8 to the isolated ground 86 of the oscillator 58. The isolated ground 86 is also connected to a patch electrode worn by the patient.

As FIG. 7 also shows, the host processor 60 also conditions the first switch element 66 to direct AC current flow from the oscillator 58 in parallel to all the electrodes 24 in the topmost electrode set E1. The AC current flows mostly through the blood pool in the heart chamber.

The host processor 60 also conditions the second switch element 72 to couple one selected electrode 24 in the second set E2 to the inverting input of the differential amplifier 70. The amplifier 70 subtracts the electrical potential measured by the selected electrode 24 in set E2 from the electrical potential measured by the ablation electrode 36. The differential potential times the gain of the amplifier 70 constitutes the input to the rectifier 76.

The rectifier 76 senses the synchronization of the phase of its input voltage relative to the phase of the oscillator 58, while the detector 78 senses the peak voltage. This signed analog value is passed through the sample and hold element 80, converted to a digital format by the converter 82 and registered by the host processor 60 in association with the identity of the electrode set E2.

The host processor 60 next conditions the second switch element 72 to couple a selected one of the electrodes 24 in next electrode set E3 to the inverting input of the amplifier 70 to derive an output voltage signal for that set E3. The host processor 60 processes the signal for set E3 in the same fashion as the output voltage signal for set E2. The processor 60 proceeds in like fashion sequentially through all the remaining electrode sets E4; E5; E6; and E7, deriving and processing the output voltage signal for each set. The processor 60 registers the digitally converted peak voltages and phase synchronization for each electrode set.

In the arrangement shown in FIG. 7, electrical capacitances and inductances of the blood pool are minimal. Therefore, the synchronization of the phase of the output voltage signal of the amplifier 70 relative to the phase of the oscillator 58 will vary depending upon whether the ablation electrode 36 is located vertically above or vertically below the set of electrodes 24 then-coupled to the inverting input of the amplifier 70.

If the electrode set is located vertically above the position of the ablation electrode 36 (as FIG. 7 shows for electrode sets E1 to E3), the output voltage signal of the amplifier 70 will be out of phase with respect to the phase of the oscillator 58 (i.e., that analog signal received by the sample and hold element 80 will have a (−) sign). This is because the potential of the ablation electrode 36 sensed at the noninverting input of the amplifier 70 (during the positive phase of oscillator output) will be more negative than the potential sensed at vertically higher electrode sets, which are sensed at the inverting input of the amplifier. As long as the potential of the ablation electrode 36 remains more negative under these conditions, the output voltage signal of the amplifier 70 remains negative, indicating an out of phase condition.

If the electrode set is located vertically below the position of the ablation electrode 36 (as FIG. 7 shows for sets E4 to E8), the output voltage signal of the amplifier 70 will be in phase with respect to the phase of the oscillator 58. This is because the potential of the ablation electrode 36 sensed at the noninverting input of the amplifier 70 (during the positive phase of oscillator output) will be more positive than the potential at lower set of electrodes sensed at the inverting input of the amplifier 70. As long as the potential of the ablation electrode 36 remains more positive under these conditions, the output voltage signal of the amplifier 70 remains positive, indicating an in phase condition.

The host processor 60 determines where the output of the peak detector 78 changes sign, by turning from (−) to (+) or vice versa. In FIG. 7, this transition occurs between electrode planes E3 and E4. This transition point fixes the i index of the ablation electrode 36 at i=3, which is the horizontal sector where the ablation electrode 36 is located.

(ii) Determining the j Index

The host processor 60 of the element 48(1) can determine the j index either by amplitude sensing or by phase sensing.

(a) Differential Amplitude Sensing

In determining the j index of the ablation element 36 using amplitude sensing (see FIG. 8), the host processor 60 conditions the first switch element 66 to direct AC current flow from the oscillator 58 to all the electrodes on one selected spline (S1) to all the electrodes in the diametrically opposite spline (S5), which are, in turn coupled by the switch element 66 to the isolated patient ground 86. The AC current thus flows horizontally from the spline Si through the blood pool in the heart chamber to the opposite spline S5.

The host processor 60 conditions the second switch element 72 to couple all the electrodes 24 in the opposite spline S5 to the inverting input of the differential amplifier 70 while the ablation electrode 36 is coupled to the noninverting input of the amplifier 70. The amplifier subtracts the electrical potential measured at the electrodes in the opposite spline S5 from the electrical potential measured at the ablation electrode 36. The differential potential times the gain of the amplifier 70 constitutes the input to the rectifier 76.

The detector 78 senses the peak voltage of the signal. The output of the peak detector 78 is passed through the sample and hold element 80 and converted to digital format by the converter 82. This digitally converted peak voltage, in association with the spline S5 then coupled to the amplifier 70, is registered by the host processor 60.

The host processor conditions the first and second switch elements 66 and 72 to proceed sequentially in this fashion coupling opposed pairs of splines in succession between the oscillator 58 and inverting input of the amplifier 70—proceeding, for example, (S2, S6); (S3, S7); (S4, S8); (S5; S1); (S6, S2); (S7, S3); and (S8, S4)—while registering the sensed peak voltage in association with the spline then-coupled to the amplifier 70.

The largest peak voltage sensed identifies the spline closest to the ablation electrode. The j index is the sector which that spline bisects.

Figure 8:
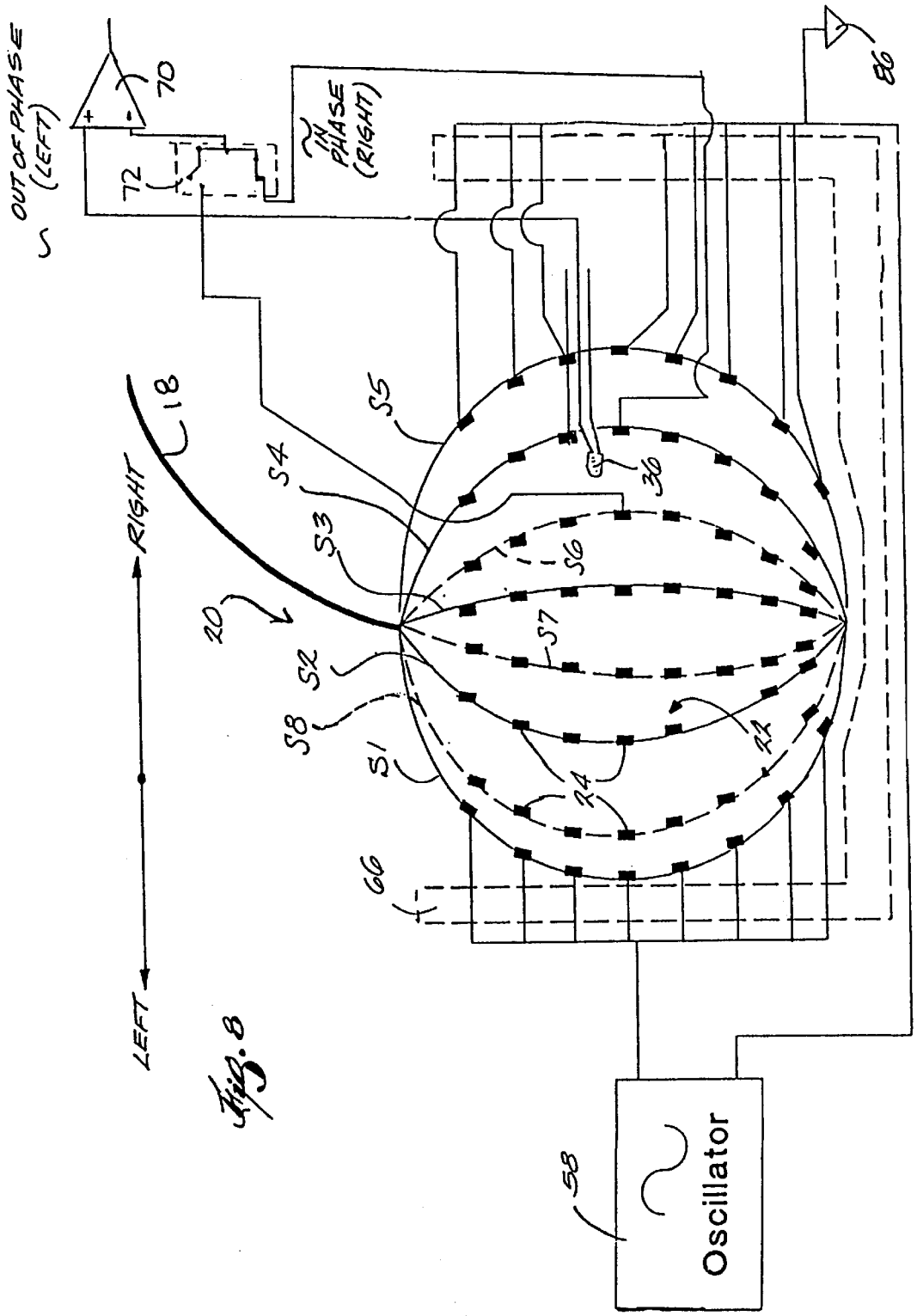
FIG. 8 is a schematic view of the use of the element shown in FIG. 4 for determining the j index.

In FIG. 8, the j index points to j=4, which locates the ablation electrode 36 in the sector bisected by the spline S4 (see also FIG. 6A).

(b) Differential Phase Sensing

Alternatively, the j index can be derived by sensing differential phase shifts, similar to the manner in which the i index was derived.

As in differential amplitude sensing, the host processor 60 conditions the first switch element 66 to direct AC current flow from the oscillator 58 from all the electrodes 24 along one selected spline (e.g., S1) to all the electrodes 24 along the diametrically opposite spline (e.g., S5), which are, in turn, coupled to the isolated patient ground 86. The host processor 60 conditions the second switch element 72 to sequentially couple electrodes 24 on the remaining splines (e.g., S2 to S4 and S6 to S8) in succession to inverting input of the differential amplifier 70, while coupling the ablation electrode to the noninverting input. The amplifier subtracts the electrical potential measured by the electrode 24 coupled to the inverting input from the electrical potential measured by the ablation electrode 36. The differential potential times the gain of the amplifier 70 constitutes the input to the rectifier 76.

The detector 78 senses the peak voltage, and the rectifier 76 senses the synchronization of the phase of the voltage signal relative to the phase of the oscillator 58. The host processor 60 registers the peak voltage and the synchronization in association with the i index of the selected electrode and the spline that carries the selected electrode.

The synchronization of the phase of the output voltage signal of the amplifier 70 relative to the phase of the oscillator 58 will vary depending upon whether the ablation electrode 36 is located horizontally to the left or horizontally to the right of the selected electrode 24 coupled to the inverting input of the amplifier 70. The peak amplitude will vary according to the proximity of the selected electrode 24 to the ablation electrode 36.

If the electrode 24 is located horizontally to the left of the position of the ablation electrode 36, the output voltage signal of the amplifier 70 will be out of phase with respect to the phase of the oscillator 58. This is because the potential of the ablation electrode 36 sensed at the noninverting input of the amplifier 70 will be more negative than the potential sensed at an electrode 24 horizontally to the left of it, which is sensed at the inverting input of the amplifier 70 (during the positive phase of oscillator output). As long as the potential of the ablation electrode 36 remains more negative under these conditions, the output voltage signal of the peak detector 78 remains negative, indicating an out of phase condition.

Likewise, if the electrode 24 is located horizontally to the right of the position of the ablation electrode 36, the output voltage signal of the amplifier 70 will be in phase with respect to the phase of the oscillator 58. This is because the potential of the ablation electrode 36 sensed at the noninverting input of the amplifier 70 will be more positive than the potential sensed at an electrode 24 horizontally to the right of it, sensed at the inverting input of the amplifier 70 (during the positive phase of oscillator output). As long as the potential of the ablation electrode 36 remains more positive under these conditions, the output voltage signal of the peak detector 78 remains positive, indicating an in phase condition.

By analyzing the change in the sign of the voltage signal from (−) to (+) or vice versa, the host processor 60 determines the left-right orientation of the electrodes 24 relative to the ablation electrode. The larger peak voltage amplitude identifies the closest spline, thereby identifying the j index.

(iii) Determining the k Index

As FIG. 6A shows, the derived i index (i=3) and the derived j index (j=4) point to one pie-shaped region 52 within the basket structure 20. This region is bisected by spline S4 and located between the set E3 and the set E4 of electrodes 24, which will be called the "region electrodes."

The k index further points to the position of the ablation electrode 36 within the region 52 in terms of its radial distance from the center axis 54. In FIG. 6A, the different radial distances are delineated along iso-radial arcs A1 to A8 extending through the region 52. The region pointed to by the k index k=1 lies between the centerline 54 and arc A1. Regions pointed to by the k index k≧2 lies between arc A(k) and A(k−1). For example, the region pointed to by the k index k=5 lies between arc A5 and A4.

The host processor 60 determines the k-index region based upon the digitally converted peak registered when the j index was derived.

The peak voltage sensed by the detector 78 varies according to the proximity of the ablation electrode 36 to the region electrodes 24. The peak voltage is largest when the ablation electrode is immediately adjacent to the region electrodes 24. The peak voltage is smallest when the ablation electrode 36 is immediately adjacent to the region electrodes that are diametrically oppositely spaced from the region electrodes 24 (which, in FIG. 6A, are the set E3 and set E4 electrodes on the opposite spline S8 (j=8)). The peak voltage will have an intermediate value when the ablation electrode 36 is immediately adjacent the center axis 54. The variations of peak voltage within a basket structure 20 for a given output voltage of the oscillator 58 can be determined empirically. These variations can also be predicted by finite element analysis.

In the illustrated and preferred embodiment, the variations in peak voltage are normalized with respect to the output voltage of the oscillator 58. The normalized voltages range from zero, at the electrodes diametrically opposite to the region electrodes, to 1.0 at the region electrodes. The normalized voltage at the center axis 54 (midway between these electrodes) will thus be 0.5.

As FIG. 6B shows, the normalized distribution of voltages within the basket structure 20 can be arranged along lines of equal voltages (iso-voltage lines). As FIG. 6B also shows, the iso-radial arcs Al to AS and the k-index regions K=1 to 8 (delineated in FIG. 6A) can be overlaid upon the normalized iso-voltage lines.

The normalized distribution of voltages shown in FIG. 6B for region (i=3, j=4) exists in all regions 52 pointed by the j indices j=1 to 8 and the i indices i=1 to 7. Therefore, the normalized distribution pattern shown in FIG. 6B can be oriented with respect to any region 52 and aligned with prescribed iso-radial arcs defined in the region.

FIG. 6B shows the normalized distribution in shades of black, white, and grey. Actually, in the preferred implementation, the normalized distribution would be in shades of color. For example, the region with the highest peak voltage is colored red (where the set E3 and E4 electrodes on the spline S4 are located). The red color blends into yellow in the next adjacent region and then blends into changing hues of green, from lighter to darker, toward the center of the display. Proceeding from the center toward the diametrically opposite electrodes (i.e., toward the set E3 and E4 electrodes on the spline S8), the green hues change to different hues of blue, from lighter to darker. The region with the smallest peak voltage (next to the set E3 and E4 electrodes on the spline S8) is colored dark blue.

The symmetric overlap between the iso-radial arcs A1 to A8 and the normalized iso-voltage lines within any region 52 of the basket structure 20 (as FIG. 6B shows) can be expressed in "look-up" table form, to derive the k index based upon normalized sensed voltage readings, as follows:

| Normalized Sensed Voltage | k index |
|---|---|
| 0.5 (Center) to 0.575 (A1) | 1 |
| 0.575 (A1) to 0.61 (A2) | 2 |
| 0.61 (A2) to 0.62 (A3) | 3 |
| 0.62 (A3) to 0.63 (A4) | 4 |
| 0.63 (A4) to 0.64 (A5) | 5 |
| 0.64 (A5) to 0.70 (A6) | 6 |
| 0.70 (A6) to 0.75 (A7) | 7 |
| 0.75 (A7) to 1.0 (A8) | 8 |

In the preferred embodiment, the host processor 60 includes a look-up table in the general form shown above. In operation, the host processor 60 registers (in absolute terms) the peak voltage sensed by the ablation electrode during the determination of the j index. The host processor 60 normalizes this sensed absolute peak value with respect to the amplitude of the voltage supplied by the oscillator 58. The host processor 60 compares the sensed normalized value to the values contained in the look-up table to derive the k index.

FIG. 6A assumes that the sensed normalized value lies in the range between 0.64 V and 0.70 V, so the k index derived from the look-up table is k=6. This derived k index k=6, along with the derived i index i=3 and the derived j index j=4, locates the position of the ablation electrode 36 at region (i=3, i=4, k=6), which points to a particular arcuate zone 56 within the space 22 defined by the basket structure 20.

The number of iso-voltage arcs A(k) contained in a given region can be more than 8 or less than 8, depending upon the degree of resolution desired. Of course, the more k indices provided within the region, the greater the resolution will be.

The method for locating the ablation electrode 36 described above relies upon applying excitation between different groups of electrodes 24 and sensing voltages with the ablation electrode 36. It should be appreciated that variations of this method (e.g., given by the reciprocity theorem applied to quadruple-ports) likewise embodies the spirit and features of the invention.

(iv) Displaying the i, j, and k Indices

In the illustrated and preferred embodiment, the host processor 60 continuously derives the i, j, and k indices in real time in the manner just described. The host processor 60 preferably outputs the derived i, j, and k indices to the real time display device 50 for viewing by the physician.

More particularly, the host processor 60 computes the location of the sensing electrodes 24 in a three dimensional coordinate system. In the preferred embodiment, a three dimensional spherical coordinate system is used, as FIG. 5A generally shows). The host processor 60 generates a three dimensional mesh within the basket surface. The points where the mesh intersect are define prescribed locations called nodes. Each node can be uniquely identified in term of an i index, a j index, and a k index.

Some of the nodes will overlie the electrodes on the basket (in the illustrated embodiment, these nodes will all have a k index of 8). The host processor 60 creates an output display 88 on the device 50 (like that shown in FIG. 9). The display 88 assigns one distinguishing indicium (for example, an asterisk) to identify the location of the electrodes 24. The display 88 also assigns other distinguishing indicia (for example, solid lines) to fill the spaces between all or some vertical sets of electrodes 24 corresponding with splines SI to S8, to give further structure and orientation to the presentation. While not shown in FIG. 9, the display 88 can also fill spaces between some or all horizontal sets of electrodes 24 corresponding with sets E1 to E8 (see FIG. 5A). The host processor 60 also preferably assigns an additional distinguishing indicium to the electrode 24 closest to the selected ablation site (for example, by circling the asterisk representing the closest electrode, as FIG. 9 shows).

The host processor 60 also assigns yet another distinguishing indicium to region 56 defined by the intersection of the derived i, j, and k indices. In FIG. 9, the intersection is bounded by lines defining a three dimensional, rectangular figure. This figure identifies the location of the ablation electrode 36.

Figure 9:
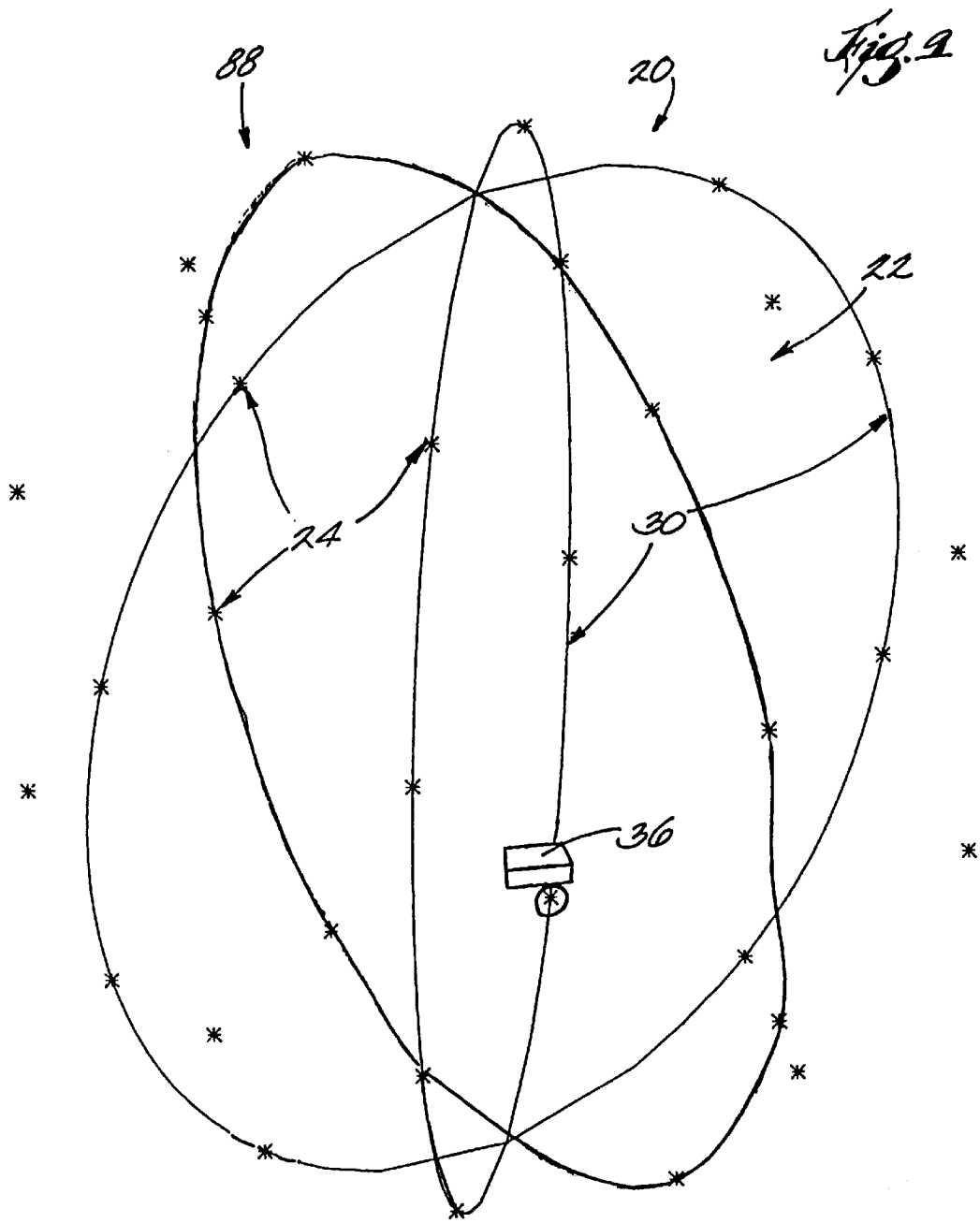
FIG. 9 is a representative real time display showing the location of the ablation electrode within the multiple-electrode structure.

By updating the display 88 continuously in real time, the processing element 48(1) aids the physician in guiding the ablation electrode 36 within the basket structure 20 toward the targeted ablation area (the circled asterisk in FIG. 9).

Figure 10:
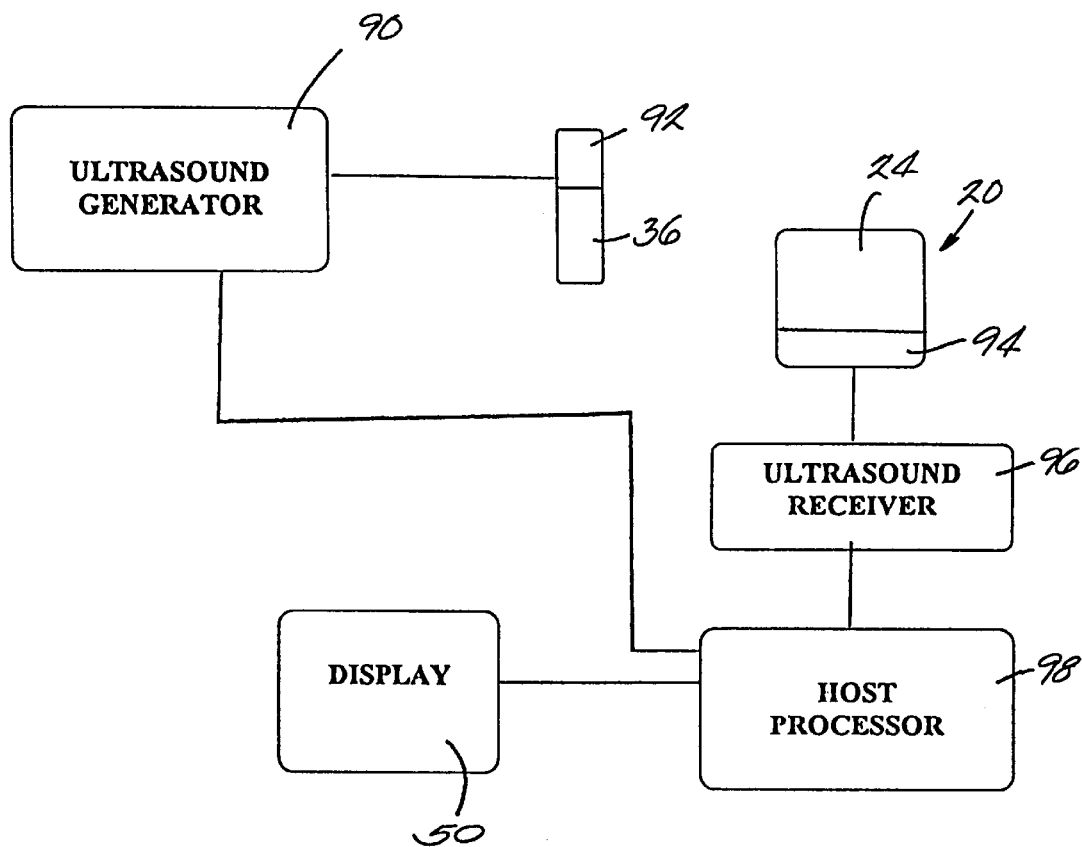
FIG. 10 is a schematic view of an element for determining the location of an ablation electrode within a multiple-electrode structure using ultrasonic time-delay sensing.

B. Ultrasound Time-Delay FIG. 10 shows an alternative implementation of the processing element, designated 48(2). In this implementation, the element 48(2) generates an ultrasonic field within the interior space 22 of the basket structure 20 between the ablation electrode 36 and the electrodes 24. The element 48(2) analyzes the ultrasonic information to locate the position of the ablation electrode within the space 22.

The element 48(2) includes an ultrasound generator 90 coupled to an ultrasound transducer 92 carried on or near the ablation electrode 36. The transducer 92 can take the form of a phased array of piezoelectric crystals that produce a planar wave form. Alternatively, the transducer 92 may be a single piezoelectric crystal, as the precise localization of the ultrasonic wave form is not required in the illustrated implementation of the element 48(2). Breyer et al. U.S. Pat. No. 4,706,681 discloses examples of the transducer 92 that can be used in association with the element 48(2).

The element 48(2) also includes small compact ultrasound transducers 94 placed on or adjacent to the electrodes 24. The transducers 94 are coupled to an ultrasound receiver 96.

The element 48(2) also includes a host processor 98. The processor 98 directs the transmission by the transducer 92 of an ultrasonic field within the space 22. The receiver 96 detects the receipt by each transducer 94 of the ultrasonic pulses emitted by the transducer 92. The host processor 98 analyzes the detected ultrasonic pulses and calculates the time delays for the transducer 94 associated with each electrode 24. Given the time delays and the known velocity of sound in the blood pool, the host processor 98 derives the distance between each electrode 24 and the ablation electrode 36.

The host processor 98 preferably employs triangulation based upon distances to develop a three dimensional localization of the position of the ablation electrode 36. The host processor 98 continually performs this detect and triangulate process for real time guidance of the ablation electrode within the basket structure space 22.

Preferably, the processor 98 also generates the spherical three dimensional discrete coordinate display .88, like that shown in FIG. 9, to display the processed ultrasonic information on the display device 50. As used to display the i, j, and k indices in the implementation of element 48(1), the display 88 shows the location of the electrodes 24, other structure of the basket 20 (for example, splines), and the targeted ablation area. The triangulation process of the element 48(2) provides a data set equivalent to the i, j, and k indices derived by the element 48(1), which can also be displayed in the manner shown in FIG. 9.

Thus, the display 88 graphically shows processed ultrasonic information in real time. This allows the physician to progressively maneuver the ablation electrode 36 within the basket structure 20 while viewing the location of the electrode 36 relative to the targeted ablation area.

C. Contact/Impedance sensing

Voltage phase and amplitude sensing by the element 48(1) and ultrasound time-delay sensing by the element 48(2) determine the approximate position of the ablation electrode 36 within the basket structure space 22, as best the spacial accuracy of the i, j, and k indices or the sensitivity of the ultrasound receivers can provide. Greater accuracy may be required to aid the physician in guiding the ablation electrode to the precise location targeted for ablation within the heart.

The elements 48(1) and 48(2) can each additionally employ impedance sensing to indicate when the ablation electrode is in very close proximity to (for example, within 1 to 2 mm) or actually touching the electrode 24 closest to the ablation site. Impedance sensing can be used with either voltage phase/amplitude sensing or ultrasound time-delay sensing, thereby augmenting general real time guidance with great accuracy to finally locate the ablation electrode 36 in the precise location identified for ablation.

Figure 11:
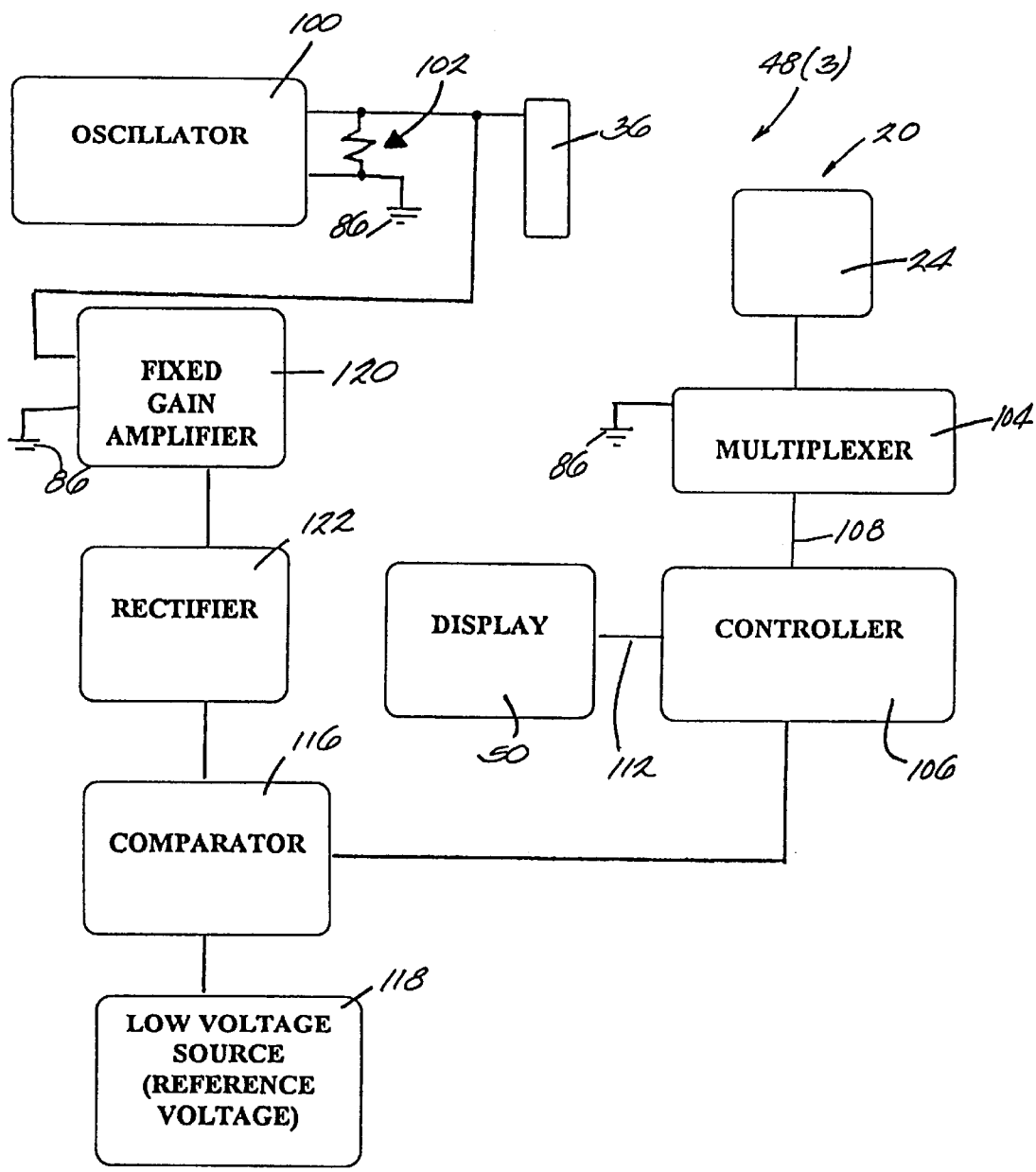
FIG. 11 is a schematic view of an element for determining the location of an ablation electrode within a multiple-electrode structure using impedance sensing.

FIG. 11 shows an element 48(3) for implementing impedance sensing for locating purposes. The element 48(3) includes an oscillator 100, which provides a constant, relatively small current (which can range between 0.1 mAmp to about 5 mAmp, and preferably is about 4–5 mAmp) at a selected frequency (which can range from about 5 kHz to 100 kHz, and preferably is about 16 kHz). Currents substantially above about 5 mAmp and frequencies substantially below 5 kHz pose the danger of inducing fibrillation.

The oscillator 100 is coupled to the ablation electrode 36 and to a dummy resistor load 102 (which is in the neighborhood of about 1.0 kOhm). This resistor load 102 is coupled at the other end to the isolated patient ground 86, already described. Further details of the purpose of the dummy resistor load 102 will be described later. The oscillator 100 injects current having a zero d.c. component through the ablation electrode 36.

The element 48(3) includes a multiplexer (MUX) 104 electrically coupled to each electrode 24. A controller 106 is also electrically coupled to the MUX 104 via an address/control bus 108. The controller 106 operates the MUX 104 to switch in sequence each electrode 24 to the isolated patient ground 86. The controller 106 is also coupled via another address control bus 112 to the output display device 50 (e.g., a CRT, LED display, or a printer).

The element 48(3) also includes a comparator 116. The comparator 116 receives input from a desired threshold low voltage source 118 (e.g., one which supplies a voltage in the neighborhood of 1.0 volt). The comparator 116 also receives as input the voltage drop between the ablation electrode 36 and ground 86 as the MUX 104 switches in sequence through the electrodes 24. The voltage drop is amplified by a fixed gain amplifier 1:20 (e.g., having an amplification factor of about X2 to X3) and rectified by a rectifier 122, which presents the peak amplitude value to the comparator 116.

The comparator 116 compares the threshold voltage from the source 118 to the voltage drop between the ablation electrode 36 and ground 86 for each electrode 24 switched by the MUX 104.

When the ablation electrode 36 is not sufficiently close to any electrode 24, the impedance of the blood pool (through which the constant current field emitted by the ablation electrode 36 flows) creates a higher voltage drop for each switched electrode 24. This higher voltage drop is in excess of the voltage of the threshold source 118. The comparator 116 generates no output. The higher voltage drop between the ablation electrode 36 and the electrodes 24 will persist when they are spaced too far apart for impedance purposes, even when the electrodes 24 and 36 are spaced close enough together to generate location-specific output based upon phase/amplitude sensing or ultrasonic information.

On the other hand, once the ablation electrode 36 comes in very close proximity to one of the electrodes 24 (e.g., which has experimentally been determined in the neighborhood of about 1 to 2 mm), the reduced impedance of the blood pool path creates a voltage input for the comparator 116 that is at or below the threshold voltage of the source 118. The comparator 116 generates an output when the sensed voltage drop between the ablation electrode 36 and a switched electrode 24 equals or drops below the set threshold level.

When this occurs, the controller 106 registers from the MUX 104 the particular electrode 24 at which the low voltage drop condition was created. The controller 106 identifies this array electrode on the output display 50 (with, for example, a flashing indicator and an audible prompt), thereby showing the physician the location of the ablation electrode 36 and the identified electrode 24 to be essentially the same.

During the short switching intervals of the MUX 104 (e.g., which are typically in the range of 1 micro-second or less), no electrode 24 is connected to ground 86. The impedance of the ablation electrode 36 with respect to ground 86 therefore becomes high when switching occurs, creating a transient high voltage drop condition. The dummy resistor load 102 of the oscillator limits the transient voltage, thereby preventing the onset of fibrillation.

Impedance sensing can also be used in conjunction with fluoroscopy or other direct imaging technologies to guide the ablation electrode to the precise location appropriate for ablating.

D. Conduction Delay Sensing

Figure 12:
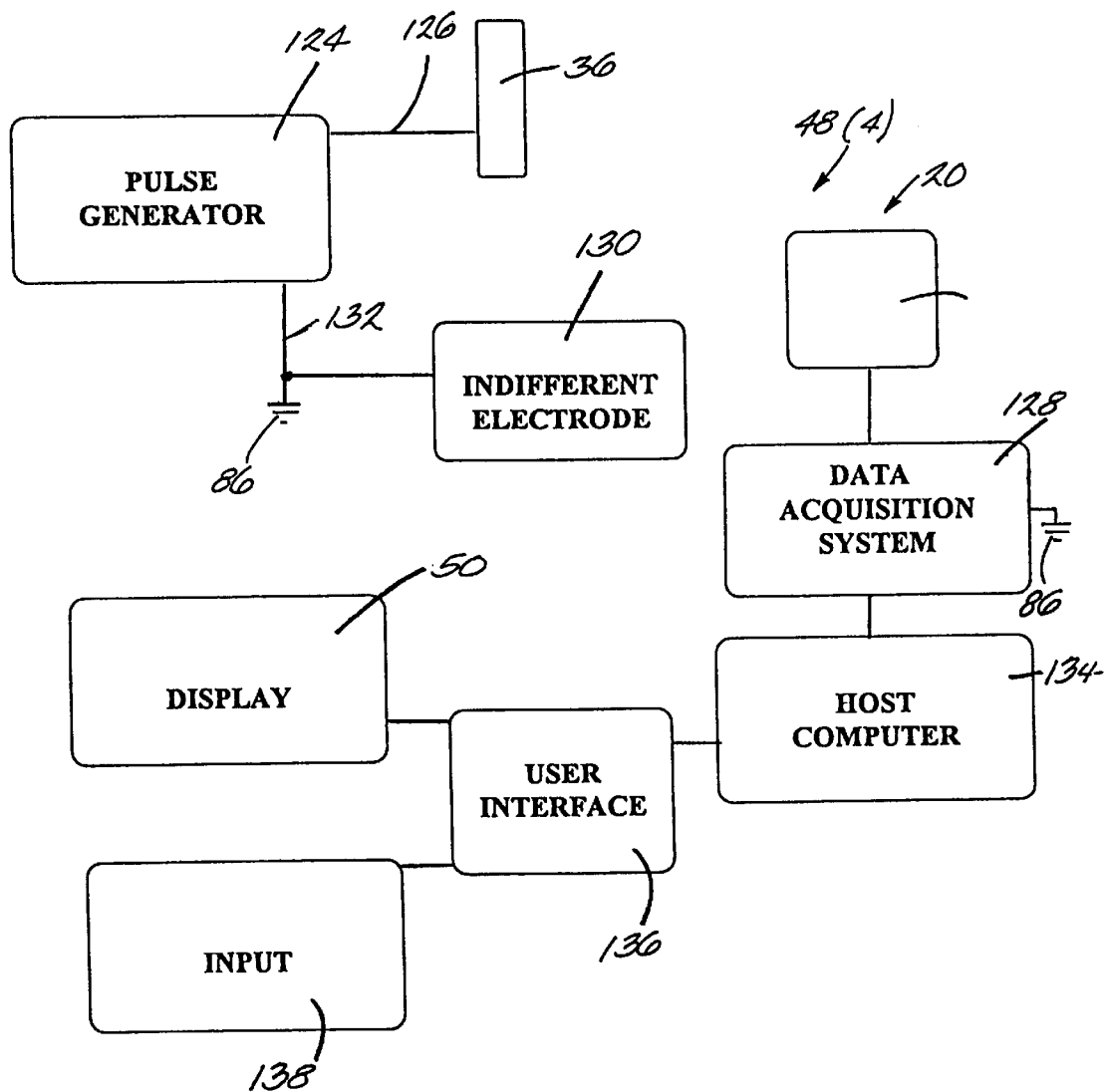
FIG. 12 is a schematic view of an element for determining the location of an ablation electrode within a multiple-electrode structure using conduction delays of depolarization events in heart tissue.

FIG. 12 shows another element 48(4) that locates the ablation electrode 36 in the basket structure 20 by sensing the timing of depolarization events in heart tissue resulting from a stimulating pacing signal.

The element 48(4) includes a pulse generator 124 having a supply path electrically coupled to the ablation electrode 36. The indifferent electrode 130 is coupled to the return path 132 of the pulse generator 124. The element 48(4) also includes a data acquisition system (DAQ) 128. The DAQ 128 is electrically coupled to the electrodes 24 and the isolated patient ground 86 (already described).

The DAQ 128 receives and processes electrical activities sensed by the electrodes 24 in the form of electrograms. A host computer 134 is coupled to the DAQ 128 for processing the electrograms to derive a location specific output.

As already described, the processing system 32 (see FIG. 1) can map the heart region to identify foci using electrograms. Therefore, in the implementation of element 48(4), the same processing system 32 that maps the heart region based upon electrograms to locate an appropriate ablation site, can also be used to locate the ablation electrode 36 within the structure 20 to carry out the ablation.

The host computer 134 also communicates with a user interface 136. The interface 136 includes the display device 50 (already described) to present the location-specific output for viewing by the physician.

In operating the system 48(4), the pulse generator 124 injects a pacing signal through the ablation electrode 36 into the myocardium contacting the ablation electrode 36. The pacing signal is returned to the pulse generator 124 by the indifferent electrode 130.

The pacing signal provides enough voltage or current to the ablation, electrode 36 to locally stimulate the myocardium. Still, the pacing signal is not large enough to field stimulate the myocardium at a distance greater than about 2 mm. In the preferred implementation, it is believed that the pacing signal should be about 3 milliamps (3 Volts), with a pulse width of about 0.5 msec.

Furthermore, the rate of the pacing signal is faster than the baseline heart beat (that is, typically greater than about 70 beats per minute). Preferably, the pacing rate should be at least 20% higher than the baseline heart beat (that is, typically greater than 84 beats per minute).

As is well known, the pacing signal depolarizes viable myocardial tissue at the site of the ablation electrode 36. The intensity of the electric field generated by the pacing signal decreases with the square of the distance from the emitting electrode 36, so the pacing signal will not be effective unless the emitting electrode 36 is very near or in intimate contact with viable myocardium. Therefore, to effectively use the element 48(4) to generate the location specific output, the physician must assure by fluoroscopy or other appropriate methodology that the ablation electrode 36 is in electrical contact with the myocardium.

The electrodes 24 will each sense an electrical event as the depolarization front generated by the pacing signal reaches them. The DAQ 128 receives the sensed electrical events, which are processed by the host computer 134 for viewing as electrograms on the display 50 (see FIG. 13, which shows four representative electrograms for illustration purposes). In conventional fashion, the DAQ 128 preferable filters or removes significant pacing artifacts that could interfere with the analysis of the electrograms.

Figure 13:
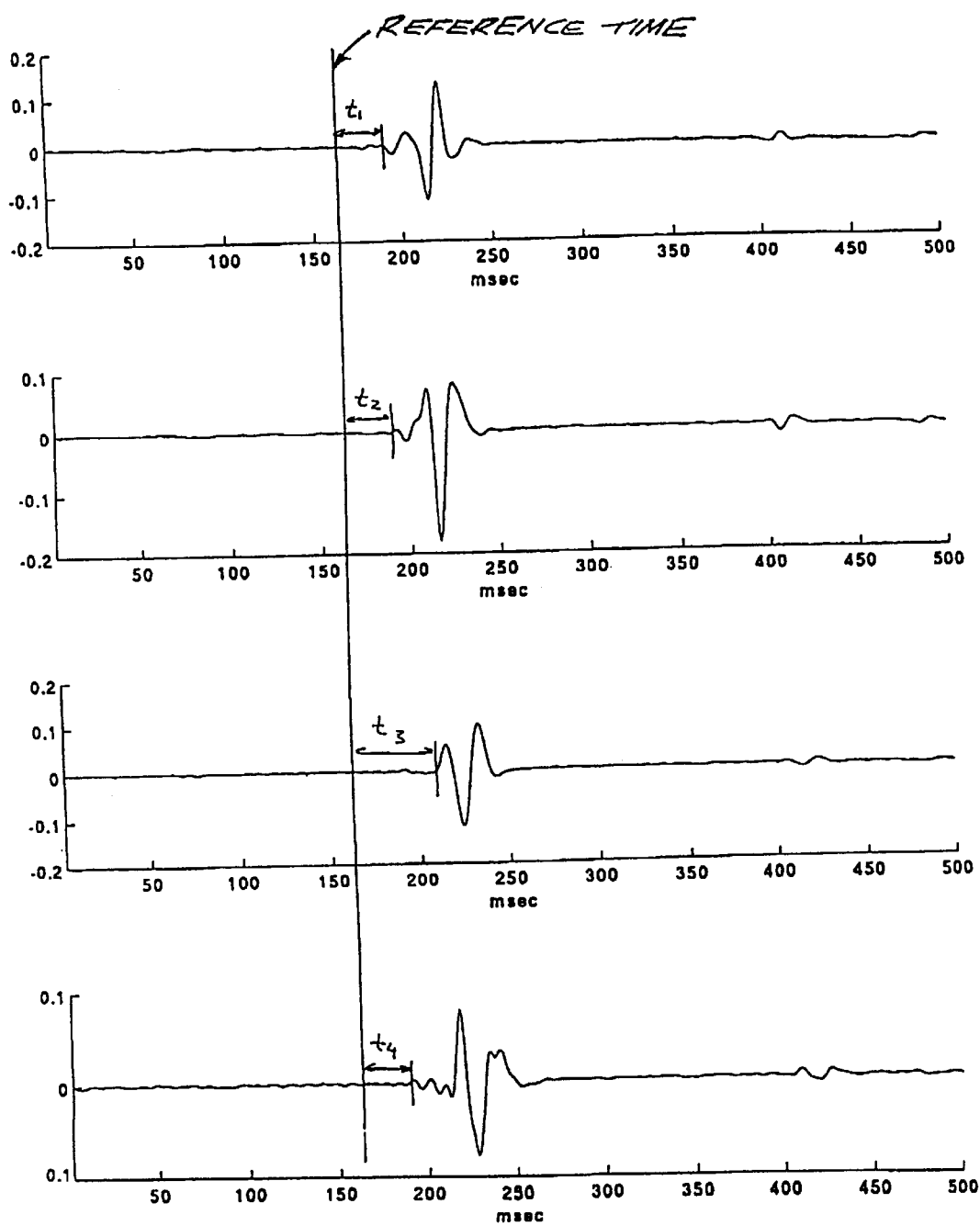
FIG. 13 is a representative view of four electrograms that have been beat clustered to derive activation time delays in conjunction with using the element shown in FIG. 12.

Analyzing the electrogram display 50 (FIG. 13), the physician manually chooses a reference time for conventional electrogram beat clustering purposes. The user interface 136 includes an input device 138 (for example, a mouse or a keyboard) for this purpose. The physician clusters the beats relative to the reference time for computing the activation delay for each electrogram, as FIG. 13 shows. The activation delay is measured between the pacing pulse and the earliest depolarization event (shown as $t_1$, $t_2$, $t_3$, and $t_4$ in FIG. 13). For all the beats in the selected cluster, the physician manually selects the earliest depolarization event for each electrode 24. The user interface 136 transmits the physician's choice to the host computer 134, which creates a matrix of the computed activation delays.

Alternatively, the host computer 134 can electronically analyze the electrograms to detect the earliest depolarization events. This implementation (not shown) includes a high pass filter to remove low frequency components from the electrograms, especially the direct current signal; a squaring function to make the signal positive; and a thresholding technique to determine the activation point. This implementation could also implement a windowing function before the thresholding function. After the activation points are determined, the host computer 134 calculates the time differences between the activation point of each electrode 24 and the activation time of the pacing pulse emitted by the ablation electrode 36. The electrode 24 having the smallest time difference between the pacing signal and its activation point is the electrode 24 nearest to the ablation electrode 36. The amplitude of the pacing artifact can also be analyzed to determine the closeness of the electrode 24 to the ablation electrode 36.

Figure 14:
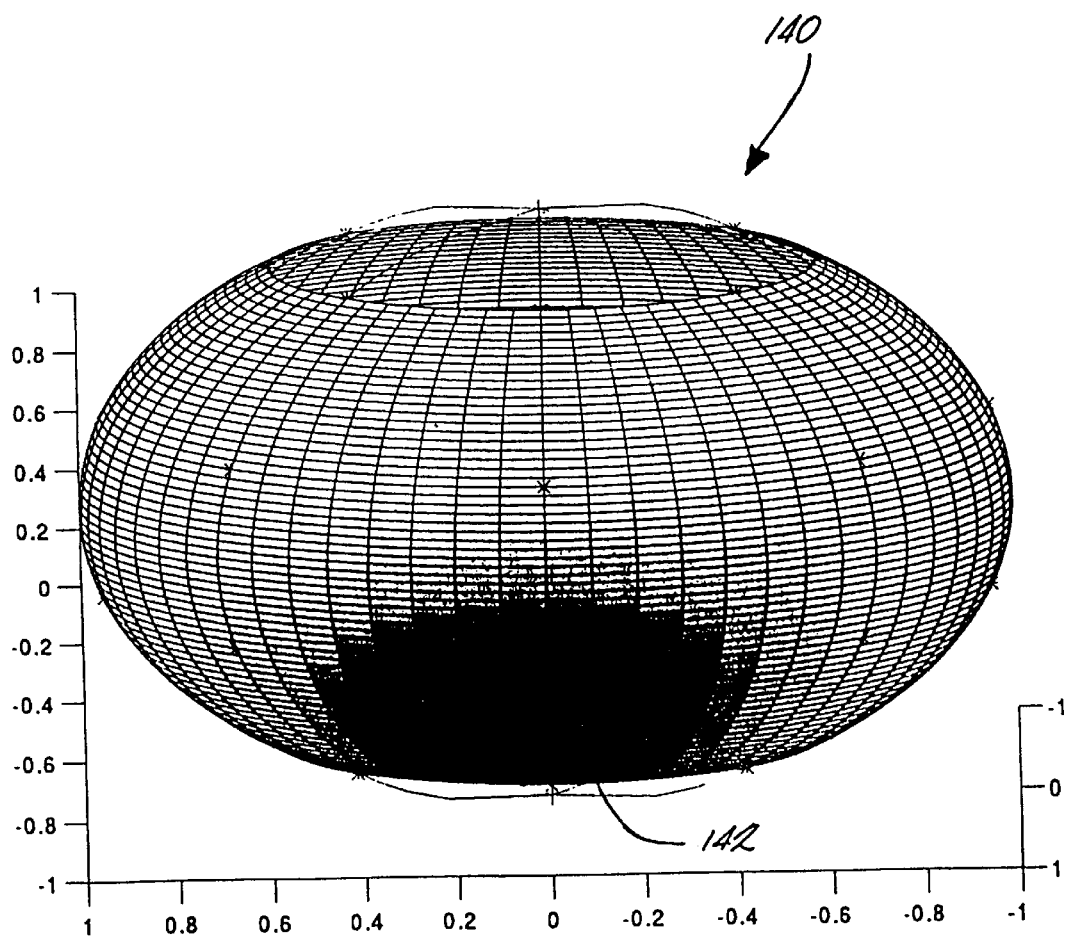
FIG. 14 is a representative iso-delay display generated by the element shown in FIG. 12 and showing the location of the ablation electrode within the multiple-electrode structure.

In the preferred embodiment (see FIG. 14), the host computer 134 creates an iso-delay display 140 of the activation times for viewing on the device 50. As FIG. 14 shows, the display 140 inherently shows the location of the ablation electrode 36 by showing the region where the least activation time delay is sensed.

In generating the display 140, the host computer 134 computes the location of the electrodes 24 in a spherical coordinate system. The system generates a three dimensional mesh upon the basket structure 20. The points where the mesh intersect are called nodes. Some of the nodes overlie the electrodes 24 on the basket structure 20. These represent knots, for which the values of the computed activation time delays are known. The values of the computed activation time delays for the remaining nodes of the three dimensional mesh have not been directly measured. Still, these values can be interpolated at each remaining node based upon the known values at each knot. Three dimensional cubic spline interpolation can be used for this purpose, although other methods can be used.

The host computer 134 assigns one color to the maximum value of the computed activation time delay. (whether actually measured or interpolated) and another color to the minimum value of computed activation time delay (again, whether actually measured or interpolated). Computer generated intermediate hues between the two colors are assigned to intermediate measured and interpolated values, based upon a linear scale.

The host computer 134 projects the generated color map upon the basket structure 20 based upon location of the nodes in the three dimensional mesh to generate the display 140. The region (identified with numeral 142 in FIG. 14) having the color assigned to the minimum activation time points to the location of the ablation electrode 36.

The element 48(4) preferably continuously updates the display 140 on a real time basis as the physician moves the ablation electrode 36 inside the basket structure 20. The continuously updated display 140 (showing movement of the region 142 in concert with movement of the ablation electrode 36) aids the physician in guiding the ablation electrode 36 to the site identified for ablation.

In an alternative implementation, the element 48(4) emits a pacing pulse through a targeted electrode 24, typically the one closest to the identified ablation site. The element 48(4) senses the electrical event generated by the pacing pulse at the ablation electrode 36. Alternatively, the ablation electrode 36 could be used as the emitter and the targeted electrode 24 as the sensor.

In either situation, the host computer 134 continuously calculates the time differences between the pacing pulse and the sensed local depolarization event, as physician moves the ablation electrode 36. As the ablation electrode 36 moves progressively closer to the targeted electrode 24, the time delays get progressively shorter, and vice versa.

Figure 15:
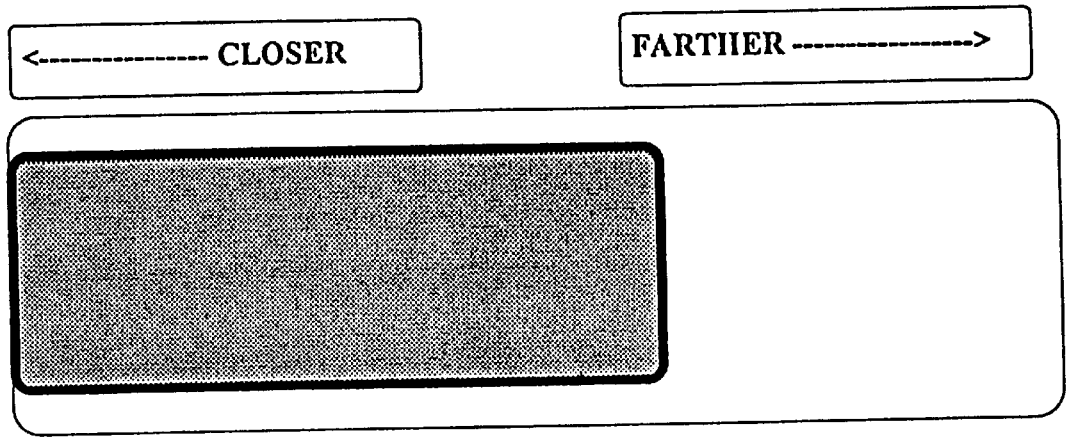
FIG. 15 is an alternative display for showing the proximity of an ablation electrode to a selected electrode based upon conduction delays of depolarization events, using the element shown in FIG. 12.

In this implementation, the host computer 134 generates a real time display 144 (see FIG. 15) showing changes in the sensed time differences as a result of moving the ablation electrode 36 relative to the targeted electrode 24. For example (as FIG. 15 shows), the display 144 depicts a bar of variable length. The bar gets longer as the time delay gets longer, indicating that the physician is moving the ablation electrode 36 away from the targeted electrode 24. Conversely, the bar gets shorter as the time delay gets shorter, indicating that the physician is moving the ablation electrode 36 toward the targeted electrode 24.

This feedback, updated continuously in real time as the physician moves the ablation electrode 36, guides the physician in locating the ablation electrode 36 at the chosen ablation site.

Various features of the invention are set forth in the following claims.

We claim:

1. A catheter system, comprising:
   an array of multiple electrodes,
   an electrode movable relative to the array,
   an emitting ultrasound transducer located adjacent one of the movable electrode and an electrode in the array;
   an ultrasound generator coupled to the emitting ultrasound transducer;
   a sensing ultrasound transducer located adjacent the other of the movable electrode and the electrode in the array;
   an ultrasound receiver coupled to the sensing ultrasound transducer; and
   a processor coupled to the ultrasound generator and the ultrasound receiver, the processor configured to provide an output that locates the movable electrode relative to the array.

2. The system of claim 1, wherein the output provided by the processor is based on a time delay between an emission of ultrasonic energy by the emitting ultrasound transducer and a sensing of the ultrasonic energy by the sensing ultrasound transducer.

3. The system of claim 1, wherein the emitting ultrasound transducer is located adjacent the movable electrode, and the sensing ultrasound transducer is located adjacent the electrode in the array.

4. The system of claim 1, further comprising a display coupled to the processor to present the output in a real time format that continuously locates the movable electrode relative to the array.

5. The system of claim 1, wherein the movable electrode is coupled to a source of ablation energy.

6. The system of claim 1, wherein the movable electrode is located on a movable catheter body.

7. A catheter system, comprising:
   an array of multiple electrodes,
   an electrode movable relative to the array,
   an emitting ultrasound transducer located adjacent the movable electrode;
   an ultrasound generator coupled to the emitting ultrasound transducer;
   a plurality of sensing ultrasound transducers, each sensing ultrasound transducer located adjacent a respective electrode in the array; and
   a processor coupled to the ultrasound generator and the ultrasound receiver, the processor configured to provide an output that locates the movable electrode relative to the array.

8. The system of claim 7, wherein the output provided by the processor is based on a time delay between an emission of ultrasonic energy by the emitting ultrasound transducer and a sensing of the ultrasonic energy by each of the sensing ultrasound transducers.

9. The system of claim 8, wherein the output is based on triangulation.

10. The system of claim 7, further comprising a display coupled to the processor to present the output in a real time format that continuously locates the movable electrode relative to the array.

11. A method for guiding a movable electrode relative to an array of multiple electrodes, comprising:
    placing the movable electrode within an interior space of the array;
    emitting ultrasonic energy from an emitting ultrasound transducer located adjacent one of the movable electrode and an electrode of the array;
    sensing the ultrasonic energy with a sensing ultrasound transducer located at the other of the movable electrode and an electrode of the array; and
    generating an output based on the sensed ultrasonic energy, the output providing information that locates the movable electrode relative to the array.

12. The method of claim 11, wherein the output is based on a time delay between an emission of ultrasonic energy by the emitting ultrasound transducer and a sensing of the ultrasonic energy by the sensing ultrasound transducer.

13. The method of claim 11, wherein the emitting ultrasound transducer is located adjacent the movable electrode, and the sensing ultrasound transducer is located adjacent an electrode of the array.

14. A method for guiding a movable electrode relative to an array of multiple electrodes, comprising:
    placing the movable electrode within an interior space of the array;
    emitting ultrasonic energy from an emitting ultrasound transducer located adjacent the movable electrode;
    sensing the ultrasonic energy with a plurality of ultrasound transducers located adjacent respective electrodes of the array; and
    generating an output based on the sensed ultrasonic energy the output providing information that locates the movable electrode relative to the array.

15. The method of claim 14, wherein the output is based on a time delay between an emission of ultrasonic energy by the emitting ultrasound transducer and a sensing of the ultrasonic energy by each of the sensing ultrasound transducers.

16. The method of claim 15, wherein the output is based on triangulation.

17. The method of claim 14, wherein the location of the movable electrode relative to the array is continuously displayed in a real time format.

18. The method of claim 14, further comprising locating the array in contact with tissue within a heart and locating foci appropriate for ablation by sensing electrical activity in the tissue.

19. A catheter assembly, comprising:
    an array of multiple electrodes having an interior space,
    an electrode movable relative to the array,
    an emitting ultrasound transducer configured for generating an ultrasonic field within the interior space, the emitting ultrasound transducer located adjacent one of the movable electrode and an electrode in the array; and a sensing ultrasound transducer configured for sensing the ultrasonic field, the sensing ultrasound transducer located adjacent the other of the movable electrode and an electrode in the array.

20. The assembly of claim 19, wherein the emitting ultrasound transducer is located adjacent the movable electrode, and the sensing ultrasound transducer is located adjacent the electrode in the array.

21. The assembly of claim 19, wherein the movable electrode and the array are located on separate catheter bodies.

22. The assembly of claim 19, further comprising a plurality of sensing ultrasound transducers configured for sensing the ultrasonic field, each of the sensing ultrasound transducers located adjacent a respective electrode of the array, and wherein the emitting ultrasound transducer is located adjacent the movable electrode.

* * * * *